(12) United States Patent
Guy et al.

(10) Patent No.: US 11,406,623 B2
(45) Date of Patent: *Aug. 9, 2022

(54) METHODS OF TREATING TUBEROUS SCLEROSIS COMPLEX WITH CANNABIDIOL AND EVEROLIMUS

(71) Applicant: GW Research Limited, Cambridge (GB)

(72) Inventors: Geoffrey Guy, Cambridge (GB); Volker Knappertz, Carlsbad, CA (US); Eduardo Dunayevich, Cambridge (GB); David Critchley, Cambridge (GB)

(73) Assignee: GW Research Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/509,939

(22) Filed: Oct. 25, 2021

(65) Prior Publication Data

US 2022/0040155 A1  Feb. 10, 2022

Related U.S. Application Data

(63) Continuation of application No. 17/188,766, filed on Mar. 1, 2021, now Pat. No. 11,160,795.

(60) Provisional application No. 62/982,506, filed on Feb. 27, 2020.

(51) Int. Cl.
| | | |
|---|---|---|
| *A61K 36/00* | (2006.01) | |
| *A61K 31/436* | (2006.01) | |
| *A61K 31/05* | (2006.01) | |
| *A61K 36/185* | (2006.01) | |

(52) U.S. Cl.
CPC ............ *A61K 31/436* (2013.01); *A61K 31/05* (2013.01); *A61K 36/185* (2013.01); *A61K 2236/15* (2013.01); *A61K 2236/17* (2013.01); *A61K 2236/333* (2013.01); *A61K 2236/37* (2013.01); *A61K 2236/39* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| | | |
|---|---|---|
| 6,403,126 B1 | 6/2002 | Webster |
| 6,949,582 B1 | 9/2005 | Wallace |
| 8,293,786 B2 | 10/2012 | Stinchcomb |
| 8,673,368 B2 | 3/2014 | Guy et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,477,019 B2 | 10/2016 | Li et al. |
| 9,522,123 B2 | 12/2016 | Whalley et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 10,092,525 B2 | 10/2018 | Guy et al. |
| 10,111,840 B2 | 10/2018 | Guy et al. |
| 10,137,095 B2 | 11/2018 | Guy et al. |
| 10,583,096 B2 | 3/2020 | Guy et al. |
| 10,603,288 B2 | 3/2020 | Guy et al. |
| 10,709,671 B2 | 7/2020 | Guy et al. |
| 10,709,673 B2 | 7/2020 | Guy et al. |
| 10,709,674 B2 | 7/2020 | Guy et al. |
| 10,765,643 B2 | 9/2020 | Guy et al. |
| 10,849,860 B2 | 12/2020 | Guy et al. |
| 10,918,608 B2 | 2/2021 | Guy et al. |
| 10,966,939 B2 | 4/2021 | Guy et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Wright et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,229,612 B2 | 1/2022 | Wright et al. |
| 2004/0110828 A1 | 6/2004 | Chowdhury et al. |
| 2005/0266108 A1 | 12/2005 | Flockhart et al. |
| 2006/0039959 A1 | 2/2006 | Wessling |
| 2007/0060638 A1 | 3/2007 | Olmstead |

(Continued)

FOREIGN PATENT DOCUMENTS

| | | |
|---|---|---|
| CA | 2 737 447 A1 | 10/2012 |
| CA | 2 859 934 A1 | 3/2016 |

(Continued)

OTHER PUBLICATIONS

[No Author Listed] Cannabidiol Therapy for Aicardi Syndrome, Aug. 2014, 4 pages.
[No Author Listed], Cannabinoid. Wikipedia. Retrieved on Jul. 9, 2015 from https://en.wikipedia.org/wiki/Cannabinoid, 15 pages.
No Author Listed], "Missouri House passes cannabis extract legislation," Kansas City Star, 2014, https://kansascity.com/news/politics-government/article346747.html, 2 pages.
[No Author Listed], Cover and Table of Contents, J Pharmacology and Exp Therapeutics, Feb. 2010, 332(2), 4 pages.

(Continued)

*Primary Examiner* — Michael V Meller
(74) *Attorney, Agent, or Firm* — Cooley LLP

(57) ABSTRACT

The present disclosure provides methods of treating tuberous sclerosis complex comprising administering cannabidiol and everolimus.

25 Claims, 5 Drawing Sheets

(56) References Cited

U.S. PATENT DOCUMENTS

| | | |
|---|---|---|
| 2007/0099987 A1 | 5/2007 | Weiss et al. |
| 2008/0119544 A1 | 5/2008 | Guy et al. |
| 2008/0188461 A1 | 8/2008 | Guan |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0183606 A1 | 7/2012 | Bender et al. |
| 2012/0202891 A1 | 8/2012 | Stinchcomb et al. |
| 2012/0270845 A1 | 10/2012 | Bannister |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0343071 A1 | 12/2015 | Vangara |
| 2015/0359756 A1 | 12/2015 | Guy et al. |
| 2016/0010126 A1 | 1/2016 | Poulos et al. |
| 2016/0166514 A1 | 6/2016 | Guy et al. |
| 2016/0166515 A1 | 6/2016 | Guy et al. |
| 2016/0220529 A1 | 8/2016 | Guy et al. |
| 2017/0007551 A1 | 1/2017 | Guy et al. |
| 2017/0008868 A1 | 1/2017 | Dialer et al. |
| 2017/0181982 A1 | 6/2017 | Guy et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Guy et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0031601 A1 | 1/2019 | ElSohly et al. |
| 2019/0083418 A1 | 3/2019 | Guy et al. |
| 2019/0160393 A1 | 5/2019 | Marshall et al. |
| 2019/0175547 A1 | 6/2019 | Stott et al. |
| 2019/0314296 A1 | 10/2019 | Wright et al. |
| 2019/0321307 A1 | 10/2019 | Guy et al. |
| 2019/0167583 A1 | 12/2019 | Shah |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206152 A1 | 7/2020 | Stott et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |
| 2020/0368179 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0093581 A1 | 4/2021 | Guy et al. |
| 2021/0169824 A1 | 6/2021 | Guy et al. |
| 2021/0177773 A1 | 6/2021 | Guy et al. |
| 2021/0244685 A1 | 8/2021 | Guy et al. |
| 2021/0267950 A1 | 9/2021 | Guy et al. |
| 2021/0290565 A1 | 9/2021 | Guy et al. |
| 2021/0330636 A1 | 10/2021 | Guy et al. |
| 2022/0000800 A1 | 1/2022 | Guy et al. |
| 2022/0008355 A1 | 1/2022 | Guy et al. |
| 2022/0023232 A1 | 1/2022 | Guy et al. |

FOREIGN PATENT DOCUMENTS

| | | |
|---|---|---|
| CN | 101040855 A | 9/2007 |
| CN | 103110582 A | 5/2013 |
| CN | 104490873 A | 4/2015 |
| DE | 10 2012 105 063 A1 | 12/2013 |
| EP | 2 578 561 A1 | 4/2013 |
| GB | 2384707 A | 8/2003 |
| GB | 2434097 A | 7/2007 |
| GB | 2434312 A | 7/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2485291 A | 5/2012 |
| GB | 2471565 B | 7/2012 |
| GB | 2478072 B | 12/2012 |
| GB | 2478074 B | 12/2012 |
| GB | 2492487 A | 1/2013 |
| GB | 2531093 A | 4/2016 |
| GB | 2531282 A | 4/2016 |
| GB | 2539472 A | 12/2016 |
| WO | WO 2002/064109 A2 | 8/2002 |
| WO | WO 2003/099302 A1 | 12/2003 |
| WO | WO 2004/016246 A1 | 2/2004 |
| WO | WO 2004/016277 A2 | 2/2004 |
| WO | WO 2004/026802 A1 | 4/2004 |
| WO | WO 2006/054057 A2 | 5/2006 |
| WO | WO 2006/133941 A2 | 12/2006 |
| WO | WO 2007/032962 A2 | 3/2007 |
| WO | WO 2007/083098 A1 | 7/2007 |
| WO | WO 2007/138322 A1 | 12/2007 |
| WO | WO 2008/019146 A2 | 2/2008 |
| WO | WO 2008/021394 A2 | 2/2008 |
| WO | WO 2008/094181 A3 | 8/2008 |
| WO | WO 2008/129258 A1 | 10/2008 |
| WO | WO 2008/144475 A1 | 11/2008 |
| WO | WO 2008/146006 A1 | 12/2008 |
| WO | WO 2009/007697 A1 | 1/2009 |
| WO | WO 2009/007698 A1 | 1/2009 |
| WO | WO 2009/020666 A1 | 2/2009 |
| WO | WO 2011/001169 A1 | 1/2011 |
| WO | WO 2011/121351 A1 | 10/2011 |
| WO | WO 2012/033478 A1 | 3/2012 |
| WO | WO 2012/093255 A1 | 7/2012 |
| WO | WO 2013/032351 A1 | 3/2013 |
| WO | WO 2014/168131 A1 | 11/2013 |
| WO | WO 2015/142501 A1 | 9/2015 |
| WO | WO 2015/184127 A2 | 12/2015 |
| WO | WO 2015/193667 A1 | 12/2015 |
| WO | WO 2015/193668 A1 | 12/2015 |
| WO | WO 2016/059399 A1 | 4/2016 |
| WO | WO 2016/059405 A1 | 4/2016 |
| WO | WO 2016/084075 A1 | 6/2016 |
| WO | WO 2016/118391 A1 | 7/2016 |
| WO | WO 2016/147186 A1 | 9/2016 |
| WO | WO 2016/022936 A1 | 11/2016 |
| WO | WO 2016/191651 A1 | 12/2016 |
| WO | WO 2016/199148 A1 | 12/2016 |
| WO | WO 2017/139496 A1 | 8/2017 |
| WO | WO 2017/168138 A1 | 10/2017 |
| WO | WO 2017/204986 A1 | 11/2017 |
| WO | WO 2018/002636 A1 | 1/2018 |
| WO | WO 2018/002637 A1 | 1/2018 |
| WO | WO 2018/002665 A1 | 1/2018 |
| WO | WO 2018/037203 A1 | 3/2018 |
| WO | WO 2019/020738 A1 | 1/2019 |

OTHER PUBLICATIONS

Afinitor® (everolimus) tablets, for oral use, and Afinitor Disperz® (everolimus tablets for oral suspension) Prescribing Information, 2009, 49 pages.

Alger, "Not too excited? Thank your endocannabinoids," Neuron, 51(4):393-595 (2006).

Ames et al., "Anticonvulsant effect of cannabidiol," S Afr Med J., 69(1):14 (1986), 1 page.

(56) References Cited

OTHER PUBLICATIONS

American Epilepsy Society, "Three Studies Shed New Light on the Effectiveness of Cannabis in Epilepsy," Oct. 14, 2014, 2 pages.
Arain, "Pregabalin in the management of partial epilepsy," Neuropsychiatr Dis Treat., 5:407-413 (2009); Epub Aug. 20, 2009.
Arslan, A. & Tirnaksiz, F., "Self-emulsifying Drug Delivery Systems," F ABAD J Pharm Sci, 38(1):55-64 (2013).
Arimanoglou et al., "All children who experience epileptic falls do not necessarily have Lennox-Gastaut syndrome . . . but many do," Epileptic Discord, 13:S3-S13 (2011).
Avoli et al., "Cellular and molecular mechanisms of epilepsy in the human brain," Prog Neurobiol., 77(3):166-200 (2005).
Bakhsh, "Pregabalin in the management of partial epilepsy," Miftaah-al-Khazaain, 1930:607-608, with English translation, 4 pages.
Bancaud, "Proposal for Revised Clinical and Electroencephalographic Classification of Epileptic Seizures," Epilepsia, 22(4):489-501 (1981).
Banerjee et al., "Case Report: Aicardi syndrome: A report of five Indian cases," Neurology India, 54(1):91-93 (2006).
Barker-Haliski et al. "How Clinical Development Can, and Should Inform Translational Science," Neuron, 84:582-593 (2014).
Benowitz et al. "Metabolic and Psychophysiologic studies of cannabidiol hexobarbital interaction," Clin Pharmacol Ther., 28(1):115-120 (1980).
Bertram, "The Relevance of Kindling for Human Epilepsy," Epilepsia, 48(Suppl. 2):65-74 (2007).
Bhatt, V. P. & Vashishtha, D. P., "Indigenous plants in traditional healthcare system in Kedarnath valley of western Himalaya," Indian J Tradit Knowl., 7(2):300-310 (2000).
Bhattacharyya et al., "Modulation of mediotemporal and ventrostriatal function in humans by Delta9-tetrahydrocannabinol: a neural basis for the effects of Cannabis sativa on learning and psychosis," Arch Gen Psychiatry, 66(4):442-451 (2009); doi:10.1001/archgenpsychiatry.2009.17.
Bipolar Health Group (Charlotte's Web Hemp Remedy, available online at http:/bipolarhealthgroup.org/index.php/charlottes-web-hemp-remedy/, accessed Sep. 6, 2017, 6 pages.
Booth, "Legalization's opening of medical pot research is dream and nightmare," Denver Post, Dec. 14, 2013, 6 pages.
Bostanci, M. O. & Bagirici, F., "The effects of octanol on penicillin induced epileptiform activity in rats: an in vivo study," Epilepsy Research, 71:188-194 (2006).
Braida, et al., "Post-ischemic treatment with cannabidiol prevents electroencephalographic flattening, hyperlocomotion and neuronal injury in gerbils," Neuroscience Letters., 346:61-64 (2003).
Brown et al., "Child Neurology Foundation, LGS" (Lennox-Gastaut Syndrome), available at http://www.childneurologyfoundation.org/disorders/lgs-lennox-gastaut-syndrome, 2019, 7 pages.
Brust, J. C. M. et al., "Marijuana use and the risk of new onset seizures," Trans Am Clin Climatol Assoc., 103:176-181 (1992).
Carlini et al., "Hypnotic and antiepileptic effects of cannabidiol," J Clin Pharmacol., 21:417S-427S (1981).
Charlotte's Web [online], "When to expect Results from CW Hemp Oil," Mar. 13, 2017, retrieved on May 21, 2018, URL https://www.cwhemp.com/blog/expecting-results-from-hemp, 6 pages.
Charlotte's Web [online], "Whole-Plant Phyto-Cannabinoids Outperform Single Molecular Compounds," Charlotte's Web Stanley Brothers, URL https://www.charlottesweb.com/blog/whole-plant-cw-hemp-cannabinoids, Dec. 18, 2019, 3 pages.
Castel-Branco et al. "The Maximal Electroshock Seizure (MES) Model in the Preclinical 98. Assessment of Potential New Anti epileptic Drugs," Methods Find Exp Clin Pharmacol., 31 (2); 101-106, 2009.
ChildNeurologyFoundation.org [online], "Disorder Directory: Learn from the Experts—LGS (Lennon-Gastaut Syndrome)," Child Neurology Foundation, available on or before Sep. 6, 2015, retrieved on May 21, 2018; URL http://www.childneurologyfoundation.org/disorders/lgs-Lennon-gastaut-syndrome, 10 pages.

2 to 20 years: Girls Stature-for-age and Weight-for-age percentiles; www.cdc.growthcharts, May 30, 2000 (accessed Apr. 11, 2019), 2019, 1 page.
Chiron, C. & Dulac, O., "The Pharmacologic Treatment of Dravet Syndrome," Epilepsia, 52 (Suppl. 2):72-75 (2011).
Chiu, P. et al., "The Influence of Cannabidiol and Δ-Tetrahydrocannabinol on Cobalt Epilepsy in Rats," Epilepsia, 20:365-375 (1979).
Chou, "Theoretical basis, experimental design, and computerized simulation of synergism and antagonism in drug combination studies," Pharmacol Rev., 58(3):621-681 (2006).
Clinical Trials.gov [online], Identifier: NCT02544750, "An open-label Extension Trial of Cannabidiol (GWP42003-P, CBD) for Seizures in Tuberous Sclerosis Complex (GWPCARE6)," Sponsor: GW Research Ltd, U.S. National Library of Medicine, Oct. 1, 2018; Retrieved from https://clinicaltrials.gov/ct2/show/NCT02544750, 6 pages.
Clinical Drug Interaction Studies—Cytochrome P450 Enzyme- and Transporter-Mediated Drug Interactions Guidance for Industry, U.S. Department of Health and Human Services, Food and Drug Administration, Center for Drug Evaluation and Research (CDER), Jan. 2020, 27 pages.
Conry et al., "Clobazam in the treatment of Lennox-Gastaut syndrome," Epilepsia, 50:1158-1166 (2009).
Consroe et al. "Anticonvulsant nature of marihuana smoking," JAMA, 234(3):306-307 (1975).
Consroe et al. "Anticonvulsant drug antagonism of delta9tetrahydrocannabinol-induced seizures in rabbits," Res Commun Chem Pathol Pharmacol., 16(1):1-13 (1977).
Consroe et al. "Anticonvulsant interaction of cannabidiol and ethosuximide in rats," J Pharm Pharmacol., 29(8):500-501 (1977). doi:10.1111/j.2042-7158.1977.tb11378.x.
Consroe, P. & Wolkin, A., "Cannabidiol—antiepileptic drug comparisons and interactions in experimentally induced seizures in rats," J Pharmacol Exp Ther., 201(1):26-32 (1977).
Consroe et al. "Effects of cannabidiol on behavioral seizures caused by convulsant drugs or current in mice," Eur J Pharmacol., 83(3-4):293-298 (1982).
Consroe, P. & Snider, S. R., "Chapter 2. Therapeutic Potential of Cannabinoids in Neurological disorders," Cannabinoids as Therapeutic Agents, R. Mechoulam, Ed., pp. 21-49 (1986).
Consroe et al. Chapter 12, "Potential Role of Cannabinoids for Therapy of Neurological Disorders," in Marijuana Cannabinoids: Neurobiology and Neurophysiology, Ed. L. Murphy (1992), 72 pages.
Cortesi et al. "Potential therapeutical effects of cannabidiol in children with pharmacoresistant epilepsy," Med Hypotheses, 68(4):920-921 2007). Epub Nov. 16, 2006.
Cortez & Snead, "Chapter 10: Pharmacologic Models of Generalized Absence Seizures in Rodents," Models of Seizures and Epilepsy, 111-126 (2006).
Crespel et al., "Lennox-Gastaut Syndrome," Chapter 14, in Epileptic Syndromes in Infancy, Childhood, and Adolescence, 5th Edition, ed. M. Bureau, et al., pp. 189-216.
Cunha et al. "Chronic administration of cannabidiol to healthy volunteers and epileptic patients." Pharmacology, 21(3):175-85 (1980).
Czapinski, et al. "Randomized 36-month comparative study of valproic acid (VPA), phenytoin (PHT), phenobarbital (PB) and carbamazepine (CBZ) efficacy in patients with newly diagnosed epilepsy with partial complex seizures." J Neurolog Sci., 150:S162 (1997).
Dasa et al. "Key Attributes of TKDL: Ganja," Brhat Nighantu Ratnakara (Saligramanighantubhusanam), RS/4336, vol. IV. 1997:170, with English translation, 5 pages.
Davis et al. "Antiepileptic action of marijuana-active substances," Federation Proceedings, 8:284-285 (1949).
Davis et al. "A predominant role for inhibition of the adenylate cyclase/protein kinase A pathway in ERK activation by cannabinoid receptor 1 in NIE-115 neuroblastoma cells." J Biol Chem. 278(49):48973-80 (2003). Epub Sep. 29, 2003.

(56) References Cited

OTHER PUBLICATIONS

De Oliveira, et al. "Anticonvulsant activity of β-caryophyllene against pentylenetetrazol-induced seizures." Epilepsy Behav., 56:26-31 (2016). doi: 10.1016/j.yebeh.2015.12.040.

Devinsky et al., "Cannabidiol: Pharmacology and potential therapeutic role in epilepsy and other neuropsychiatric disorders," Epilepsia, 55(6):791-802 (2014).

Dravet, "The core Dravet syndrome phenotype," Epilepsia. 52 Suppl 2:3-9. doi: 10.1111/j.1528-1167.2011.02994.x. (2011).

Dreifus et al., "Proposal for Revised Clinical and Electroencephalographic Classification of Epileptic Seizures," Epilepsie, 22:489-501 (1981).

Dulac, "Use of Lamotrigine in Lennox-Gastaut and Related Epilepsy Syndromes," J. Child Neurolog, 12(Supplement 1):S23-S29 (1997).

Dulac, "Vigabatrin in Childhood Epilepsy," J. Child Neurolog., 6(Supplement 2), S30-S37 (1991).

Eadie, "Shortcomings in the current treatment of epilepsy," Expert Rev Neurother, 12(12):1419-1427 (2012).

Ebrahimi-Fakhari, D. et al., "Cannabidiol Elevates mTOR Inhibitor Levels In Tuberous Sclerosis Complex Patients," (2020) Pediatric Neurology, 12 pages; https://doi.org/10.1016/j.pediatrneurol.2019.11.017.

Elsohly and Gul. "Constituents of Cannabis Sariva," Chapter 1, Handbook of Cannabis, ed. Roger G. Pertwee, pp. 3-22 (2014).

Ettienne De Meijer, "The Chemical Phenotypes (Chemotypes) of Cannabis," Chapter 5, Handbook of Cannabis, Handbook of Cannabis, Roger G. Pertwee (ed.), pp. 89-110 (2014).

Engel, "Report of the ILAE classification core group," Epilepsia, 47(9):1558-1568 (2006).

Engel, "Chapter 1: What Should be Modeled?" In Models Seizure Epilepsy, 2006, 14 pages.

Eggers, "Temporal lobe epilepsy is a disease of faulty neuronal resonators rather than oscillators, and all seizures are provoked, usually by stress," Med Hypotheses., 69(6):1284-9 (2007).

Epidiolex® (cannabidiol) oral solution, CV, Prescribing Information, 2018, 30 pages.

Fariello. "Parenteral Penicillin in Rats: An Experimental Model of Multifocal Epilepsy," Epilepsia, 17:217-222 (1976).

Ferdinand, et al., "Cannabis-psychosis pathway independent of other types of psychopathology," Schizophr Res., 79(2-3):289-295 (2005).

Fisher et al., "The impact of epilepsy from the patient's perspective I. Descriptions and subjective perceptions," Epilepsy Res, 41(1):39-51 (2000).

Gabor et al., "Lorazepam versus phenobarbital: Candidates for drug of choice for treatment of status epilepticus," J Epilepsy, 3(1):3-6 (1990).

Galilly et al., "Overcoming the Bell-Shaped Dose-Response of Cannabidiol by Using Cannabis Extract Enriched in Cannabidiol," Pharmacology & Pharmacy, 6:75-85 (2015).

Gardner [online], "Comes Now Epidiolex (FDA Approves IND Studies of CBD)," BeyondTHC.com, Oct. 22, 2013, retrieved on Jan. 31, 2018, URL http://www.beyondthc.com/comes-now-epidiolex-fda-approves-ind-studies-of-cbd, 4 pages.

Gastaut, "Clinical and electroencephalographical classification of epileptic seizures," Epilepsia, 11(1):102-113 (1970).

Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde_presentation.pdf, Sep. 9-11, 2014>, 45 pages.

Geffrey et al. "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings_events/annual_meeting_abstracts/view/1868979>, 2 pages.

Green, "CBD: An Unconventional Therapy," available online at http://nugs.com/article/cbd-an unconventional-therapy.html, published Mar. 24, 2014, 5 pages.

Gresham et al "Treating Lennox-Gastaut syndrome in epileptic pediatric patients with third generation rufinamide," Neuropsychiatr Dis Treat., 6:639-645, Oct. 5, 2010.

Gross et al. "Marijuana use and epilepsy: prevalence in patients of a tertiary care epilepsy center," Neurology, 62(11):2095-2097 (2004).

Guimaraes et al., "Antianxiety effect of cannabidiol in the elevated plus-maze," Psychopharmacology (Berl.), 62(11):2095-2097 (2004).

Guerrini et al., "Lamotrigine and Seizure Aggravation in Severe Myoclonic Epilepsy," Epilepsia, 39(5):508-512 (1998).

GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL https://www.gwpharm.com/about-us/news/gw-pharmaceuticals-announces-epidiolex%C2%AE-receives-fast-track-designation-fda-treatment, 2 pages.

GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.

GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.

GWPharm [online], "GW Pharmaceuticals Receives Orphan Drug Designation by FDA for Epidiolex® in the treatment of Lennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.

Heinemann et al., "An Overview of in Vitro Seizure Models in Acute and Organotypic Slices," Chapter 4, 35-44 (2006).

Hill et al. "Δ9-Tetrahydrocannabivarin suppresses in vitro epileptiform and in vivo seizure activity in adult rats," Epilepsia, 51(8):1522-1532 (2010); doi: 10.1111/j.1528-1167.2010.02523.x. Epub Feb. 26, 2010.

Hill, "Cannabidivarin-rich cannabis extracts are anticonvulsant in mouse and rat via a CB 1 receptor-independent mechanism," British Journal of Pharmacology, 170(3): 679-692 (2013).

Holmes et al., "Choosing the correct AED: From Animal Studies to the Clinic," Pediatr Neurol., 38(3):151-162 (2008).

Iannotti et al. "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability," ACS Chem Neurosci., 5(11):1131-1141 (2014); doi: 10.1021/cn5000524.

ICE Epilepsy Alliance, the Dravet Syndrome Spectrum, Nov. 2, 2008, 2 pages.

IUPHAR/BPS Guide to Pharmacology [online], "Entry for Δ 9-tetrahydrocannabidiol," available on or before Mar. 29, 2016, retrieved on Jun. 20, 2018, URL <http://www.guidetopharmacology.org/GRAC/LigandDisplayForward?tab=biology&ligandID=242>, 2 pages.

Iuvone et al., "Neuroprotective effect of cannabidiol, a non-psychoactive component from Cannabis sativa, on beta-amyloid-induced toxicity in PC12 cells," J Neurochem., 89(1):134-141 (2004).

Izzo et al., "Non-psychotropic plant cannabinoids: new therapeutic opportunities from an ancient herb," Trends in Pharmacological Sciences, 30(10):515-527 (2009).

Jacobson, "Survey of Current Cannabidiol Use in Pediatric Treatment-Resistant Epilepsy," Poster, Apr. 22, 2013, 1 page.

Jaeger, W. et al., "Inhibition of cyclosporine and tetrahydrocannabinol meabolism by cannabidiol in mouse and human microsomes," Xenobiotica, 26(3):275-284 (1996).

Jeavons et al., "Sodium valproate in treatment of epilepsy," Br Med J., 15; 2(5919):584-586 (1974).

(56) References Cited

OTHER PUBLICATIONS

Jones et al. [online], Info & Metrics / Article Information, "Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info, 9 pages.
Joy, et al. "Marijuana and Medicine. Assessing the Science Base." National Academy Press. Washington D.C. 1999. 170 pages.
Kahan et al., "Risk of selection bias in randomized trials," Trials, 16:405 (2015); doi: 10.1186/s13063-015-0920-x.
Khan et al., Key Attributes of TKDL: Nushka-e-Qutoor, Muheet-e-Azam, 1887 (with English translation), 2 pages.
Khan et al., "Key Attributes of TKDL: Sufoof-e-Qinnab Barae Waja," Khazaain-al-Adiva, 1911, (with English translation), 5 pages.
Khan et al., "Key Attributes of TKDL: Usaara-e-Qinnab Barai Qoolanj," Khazaain-al-Advia, 1911 (with English translation), 6 pages.
Khan et al., "Key Attributes of TKDL: Zimad-e-Qinnab," Khazaain-al-Adiva, 1911 (with English translation), 5 pages.
Klitgaard et al., "Electrophysiological, neurochemical and regional effects of levetiracetam in the rat pilocarpine model of temporal lobe epilepsy," Seizure, 12(2):92-100 (2003).
Klitgaard et al., "Evidence for a unique profile of levetiracetam in rodent models of seizures and epilepsy," European journal of Pharmacology, 353(2):191-206 (1998).
Kramer et al., "Febrile infection-related epilepsy syndrome (FIRES): pathogenesis, treatment, and outcome: a multicenter study on 77 children," Epilepsia, 52(11):1956-1965 (2011); doi:10.1111/j.1528-1167.2011.03250.x. Epub Aug. 29, 2011.
Kuhn et al., "Potent activity of carfilzomib, a novel, irreversible inhibitor of the ubiquitin-proteasome pathway, against preclinical models of multiple myeloma," Blood, 110(9):3281-3290 (2007).
Kwan et al., "Definition of drug resistant epilepsy: consensus proposal by the ad hoc Task Force of the ILAE Commission on Therapeutic Strategies," Epilepsia, 51(6):1069-1077 (2010); doi:10.1111/j.1528-1167.2009.02397.x.
LeafScience.com [online], "What are the Highest CBD Strains?" Oct. 15, 2014, retrieved on Feb. 16, 2017, URL www.leafscience.com/2014/10/15/highest-cbd-strains/, 2 pages.
Leino, A. et al., "Evidence of a clinically significant drug-drug interaction between cannabidiol and tacrolimus: A case report," American Journal of Transplantation, 18 (Suppl. 4): 744-745 (2018).
Leo et al., "Cannabidiol and epilepsy: Rationale and therapeutic potential," Pharmacological Research, 107:85-92 (2016).
Lewis, "Mystery Mechanisms," The Scientist.com, Jul. 29, 2016, retrieved on Nov. 8, 2017, URL <https://www.the-scientist.com/?articles.view/articleNo/46688/title/Mystery-Mechanisms/>, 2 pages.
Lieu et al., "Assessment of self-selection bias in a pediatric unilateral hearing loss study," Otolarvnzol Head Neck Surz., 142(3):427-433 (2010).
Lindamood and Colasanti, "Effects of delta 9-tetrahydrocannabinol and cannabidiol on sodium-dependent high affinity choline uptake in the rat hippocampus," J Pharmacology Experimental Therapeutics, 213(2):216-221 (1980).
Long et al., "The pharmacological actions of cannabidiol," Drugs of the Future, 30(7):747-53 (2005).
Loscher and Schmidt, "Modern antiepileptic drug development has failed to deliver: ways out of the current dilemma," Epilepsia, 52(4):657-678 (2011); doi: 10.1111/j.1528-1167.2011,03024.x.
Lowenstein, "Chapter 363: Seizures and Epilepsy," Diseases of the Central Nervous System, 2498-2512 (2008).
Lutz, "On-demand activation of the endocannabinoid system in the control of neuronal excitability and epileptiform seizures," Biochem Pharmacol, 68(9):1691-1698 (2004).
Luttjohann et al., "A revised Racine's scale for PTZ-induced seizures in rats," Physiol Behav., 98(5):579-586 (2009); doi: 10.1016/j.physbeh.2009.09.005.
Maa et al., "The case for medical marijuana in epilepsy," Epilepsia, 55(6):783-786 (2014); doi: 10.1111/epi.12610.

Mackie, "Cannabinoid receptors as therapeutic targets," Annu Rev Pharmacol Toxicol., 46:101-22 (2006).
Majoosi et al., "Key Attributes of TKDL: Saoot Baraae Sara," Kaamil-al-Sena'ah, Central Council for Research in Unani Medicine, 2005 (with English translation), 2 pages.
Malfait et al., "The nonpsychoactive cannabis constituent cannabidiol is an oral anti-arthritic therapeutic in murine collagen-induced arthritis," PNAS, 97(17):9561-9566 (2000).
Manni et al., "Obstructive Sleep Apnea in a Clinical Series of Adult Epilepsy Patients: Frequency and Features of the Comorbidity," Epilepsia, 44(6):836-840 (2003).
Manno, "Status Epilepticus: Current Treatment Strategies," The Neurohospitalist, 1(1):23-31 (2011).
Mattson et al., "Comparison of carbamazepine, phenobarbital, phenytoin, and primidone in partial and secondarily generalized tonic-clonic seizures," N. Engl. J. Med, 313(3): 145-151, Jul. 18, 1985.
Mattson et al., "Prognosis for total control of complex partial and secondary generalized tonic clonic seizures," Neurology, 47:68-76 (1996).
Mares et al., "Electrical Stimulation-Induced Models of Seizures in Model of Seizures," Chapter 12, In: Models of Seizures and Epilepsy, Philip A. Schwartzkroin & Solomon L. Moshe (eds.) 2006, 7 pages.
Marinol® Label, Unimed Pharmaceuticals, Inc., Jul. 2006, <https://www.accessdata.fda.gov/dmgsatfdadocs/label/2006/018651s025s026lbl.pdf>, 11 pages.
Martin et al., "Structure-Anticonvulsant Activity Relationships of Cannabidiol Analogs," National Institute on Drug Abuse, Research Monograph Series, 79:48-58 (1987).
McCormick et al., "On the cellular and network bases of epileptic seizures," Annu Rev Physiol, 63:815-846 (2001).
McNamara, "Chapter 19: Pharmacotherapy of the Epilepsies," Goodman & Gilman's The Pharmacological Basis of Therapeutics, 11th ed., McGraw-Hill Companies, 2006, pp. 501-525.
Mechoulam et al., "Toward drugs derived from cannabis," Naturwissenschaften, 65(4):174-179 (1978).
Medicos [online], "Convulsive Disorders and their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving>, 3 pages.
Merlis, "Proposal for an International Classification of the Epilepsies," Epilepsia, 11:114-119 (1970).
Miller et al., "Mapping genetic modifiers of survival in a mouse model of Dravet syndrome," Genes, Brain and Behavior, 13:163-172 (2014).
Moral et al., "Pipeline on the Move," Drugs of the Future, Jan. 2014, 39(1): 49-56.
Morard et al., "Conversion to Sirolimus-Based Immunosuppression in Maintenance Liver Transplantation Patients," Liver Transplantation, 13:658-664 (2007).
Morelli et al., "The effects of cannabidiol and its synergism with bortezomib in multiple myeloma cell lines. A role for transient receptor potential Vanilloid type-2," Int J Cancer, 134(11):2534-2546 (2014).
MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.
Nabissi et al., "Cannabinoids synergize with cafilzomib, reducing multiple myeloma cells viability and migration," Oncotarget, 7:77553 (2016).
Nair et al., "A simple practice guide for dose conversion between animals and human," Journal of Basic and Clinical Pharmacy, 7:27-31 (2016).
Neto et al., "The role of polar phytocomplexes on anticonvulsant effects of leaf extracts of Lippia Alba (Mill.) N.E. Brown chemotypes," J. Pharm Pharmacol., 61(7):933-9 (2009).
Ng et al., "Illicit drug use and the risk of new-onset seizures," Am J Epidemiol., 132(1):47-57 (1990).
Oakley et al., "Dravet Syndrome Insights into pathophysiology and therapy from a mouse model of Dravet syndrome," Epilepsia, 52(Suppl. 2):59-61 (2011).

(56) References Cited

OTHER PUBLICATIONS

Obay et al., "Antiepileptic effects of ghrelin on pentylenetetrazole-induced seizures in rats," Peptides, 28(6):1214-1219. Epub Apr. 19, 2007.
Olyaei, A. J. et al., "Interaction Between Tacrolimus and Nefazodone in a Stable Renal Transplant Recipient," Pharmacotherapy, 18(6):1356-1359 (1998).
Pelliccia et al., [Online], "Treatment with CBD in oily solution of drug-resistant pediatric epilepsies," 2005 Congress on Cannabis and the Cannabinoids, Leiden, The Netherlands: International Association for Cannabis as Medicine, 2005, 14, retrieved on Jun. 30, 2015, URL <http//www.cannabis-med.org/studies/ww_en_db_study_show.php?s_id=173&&search_pattern=EPILEPSY>, 2 pages, Abstract only.
Pereira et al., "Study pharmacologic of the GABAergic and glutamatergic drugs on seizures and status epilepticus induced by pilocarpine in adult Wistar rats," Neurosci Lett.., 419(3):253-257 (2007). Epub Apr. 13, 2007.
Pertwee, "Cannabinoid receptor ligands: clinical and neuropharmacological considerations, relevant to future drug discovery and development," Expert Opin Investig Drugs, 9(7):1553-1571 (2000).
Pertwee, "The diverse CB1 and CB2 receptors pharmacology of three plant cannabinoids: Alpha9 Tetrahydrocannabinol, cannabidiol and alpha9-tetrahydrocannabivarin," BR. J. Pharmacol., 153(2): 199-215 (2008).
Pertwee, "Chapter 3: The Pharmacology and Therapeutic Potential of Cannabidiol," Cannabinoids, Ed Vincenzo Di Marzo ed., 2004, pp. 32-83.
Petrocellis et al., "Effects of cannabinoids and cannabinoid-enriched Cannabis extracts on TRP channels and endocannabinoid metabolic enzymes," British Journal of Pharmacology, 163:1479-1494 (2011).
Pohl et al., "Effects of flunarizine on Metrazol-induced seizures in developing rats," Epilepsy, 1(5):302-305 (1987).
Porter et al., "Report of a parent survey of cannabidiol-enriched cannabis use in pediatric treatment-resistant epilepsy," Epilepsy Behav., 29(3):574-577 (2013).
Porter et al., "Randomized, multicenter, dose-ranging trial of retigabine for partial-onset seizures," Neurology, 68(15):1197-1204 (2007).
Poortman—Van Der Meer, "A contribution to the improvement of accuracy in the quantitation of THC," Forensic Science International, 101(1):1-8 (1999).
Potter, "Cannabis Horticulture," Chapter 4, Handbook of Cannabis, Roger G. Pertwee (ed.), pp. 65-88 (2014).
Pouton, "Lipid formulations for oral administration of drugs: non-emulsifying, self-emulsifying and 'self-microemulsifying' drug delivery systems," Eur. J. Pharm Sci, 11(Supp. 2):S93-S98 (2000).
Press et al., "Parenteral reporting of response to oral cannabis extracts for treatment of refractory epilepsy," Epilepsy Behav, 45:49-52 (2015).
Pruitt et al., "Ethanol in Liquid Preparations Intended for Children," Pediatrics, 73(3):405-407 (1984).
Raab et al., "Multiple myeloma," Lancet, 374(9686):314-339 (2009).
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi—Goutières Syndrome," Official J Eur Paediatric Neurology Society, 18:30-37 (2014).
Rauca et al., "The role of superoxide dismutase and alpha-tocopherol in the development of seizures and kindling induced by pentylenetetrazol—influence of the radical scavenger alpha-phenyl-N-tert-butyl nitrone," Brain Research, 1009(1-2):203-212 (2004).
Resstel et al. "5-HT1A receptors are involved in the cannabidiol-induced attenuation of behavioural and cardiovascular responses to acute restraint stress in rats," Br J Pharmacol., 156(1):181-188 (2009).
Rosenberg et al., "Cannabinoids and Epilepsy," Neurotherapeutics, 12(4):747-768 (2015).
Rosenkrantz et al., "Oral and Parenteral Formulations of Marijuana Constituents," J Pharm Sci, 61(7):1106-1112 (1972).
Rubio et al., "In vivo Experimental Models of Epilepsy," Central Nervous System Agents in Medicinal Chemistry, 10:298-309 (2010).
Russo, "Taming THC: potential cannabis synergy and phytocannabinoid-termoid entourage effects," British J. of Pharm., 163:1333-1364 (2011).
Sadanandasarma et al., "Key Attributes of TKDL: Suddha Bhanga Visista Gunah Aur Matra," Rasatarangini 11th Ed., 720-723 (with English translation), 8 pages.
Sander, "The epidemiology of epilepsy revisited," Curr Opin Neural, 16(2):165-170 (2003).
Sastri et al., "Key Attributes of TKDL: Vijaya Kalpah (Apasmaranasaka)," Anandakandam 1st ed., 1952:241 (with English translation), 5 pages.
Scuderi et al., "Cannabidiol in medicine: a review of its therapeutic potential in CNS disorders," Phytother Res., 23(5):597-602 (2009).
Silva et al., "Clobazam as Add-on Therapy in Children with Epileptic Encephalopathy," Can. J. Neurol. Sci., 33:209-213 (2006).
SHUKLA [online], "New Automated Purification Strategies for Scale-Up," PCISyntesis.com, posted Dec. 25, 2017, https://www.pcisynthesis.com/new-automated-purification-strategies-for-scale-up/, 5 pages.
Sperling et al., "Carisbamate as adjunctive treatment of partial onset seizures in adults in two randomized, placebo-controlled trials," Epilepsia, 51(3):333-343 (2010).
Stafstrom et al., "Models of Pediatric Epilepsies: Strategies and Opportunities," Epilepsia, 47(8):1407-1414 (2006).
Stephenson, "In Memoriam: Professor Jean Aicardi (1926-2015)," Pediatric Neurology, 54:3-4 (2016).
Stott et al., "Cannabinoids for the pharmaceutical industry," Euphytica, 140:83-93 (2004).
Strickley, "Solubilizing Excipients in Oral and Injectable Formulations," Table VIII, Pharmaceutical Research, 21(2):201-230 (2004).
Swann et al., "The effects of seizures on the connectivity and circuitry of the developing brain," Ment Retard Dev Disabil Res Rev., 10(2):96-100 (2004).
Thomas et al., "Evidence that the plant cannabinoid Delta9-tetrahydrocannabivarin is a cannabinoid CB1 and CB2 receptor antagonist," Br J Pharmacol., 146(7):917-926 (2005).
Thumma et al., "Influence of plasticizers on the stability and release of a prodrug of ./19-tetrahydrocannabinol incorporated in poly (ethylene oxide) matrices," Eur J Pharmaceutics and Biopharmaceutics, 70(2):605-614 (2008).
Thurman et al., "Standards for epidemiologic studies and surveillance of epilepsy," Epilepsia, 52 (Suppl 7):2-26 (2011).
Thurston, "Avoid Charlotte's Web for Epilepsy," Jun. 26, 2014, URL <http://drthurstone.com/charlotted-web-not-safest-option-epilepsy-treatment/>, 4 pages.
Trembly & Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.
Turkanis et al., "An Electrophysiological Analysis of the Anticonvulsant Action of Cannabidiol on Limbic Seizures in Conscious Rats," Epilepsia, 20:351-363 (1979).
U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
Usami et al., "Synthesis and pharmacological evaluation in mice of halogenated cannabidiol derivatives," Chem Pharm Bull (Tokyo), 47(11):1641-1645 (1999).
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel, "Treatment of Lennox-Gastaut Syndrome: overview and recent findings," Neuropsychiatr Dis Treat, 4(6):1001-1019 (2008).
Velasco et al., "Anticancer mechanisms of cannabinoids," Curr Oncol, 23(2):S23-S32 (2016).

(56) References Cited

OTHER PUBLICATIONS

Velisek, "Chapter 11: Models of Chemically-Induced Acute Seizures," Models of Seizures and Epilepsy, pp. 127-152 (2006).
Veliskova, "Chapter 48: Behavioral Characterization of Seizures in Rats," Models of Seizures and Epilepsy, pp. 601-611 (2006).
Vollner et al., "Haschisch XX+ [Haschisc XX+]: Cannabidivarin, a new hashish substance," Tetrahedron Letters, 10(3):145-147 (1969).
Wahle et al., "Development of Tolerance to the Anticonvulsant Effect of Valproate but not to Ethosuximide in a Rat Model of Absence Epilepsy," Eur J Pharma, 181(1-2):1-8 (1990).
Wallace et al., "Pharmacotherapy for Dravet Syndrome," Pediatr. Drugs, 18:197-208 (2016).
Wallace et al., "Assessment of the role of CB 1 receptors in cannabinoid anticonvulsant effects," Eur J Pharmacol., 428(1):51-57 (2001).
Weimer-Kruel, A. et al., "Cannabidiol Interacts Significantly with Everolimus—Report of a Patient with Tuberous Sclerosis Complex," Neuropediatrics, 50(6), 2019, 4 pages; doi:https://doi.org/10.1055/s-0039-1695786.
Weston et al., "Tetrahydrocannabivarin exhibits anticonvulsant effects in a piriform cortical brain slice model of epileptiform activity," Proceedings of the British Pharm Society, Dec. 2006, retrieved on Mar. 1, 2017, URL <http://www.pA2online.org/abstrat/abstract.jsp?abid=28533>, 1 page, Abstract only.
Wingerchuk, "Cannabis for medical purposes: cultivating science, weeding out the fiction," Lancet, 364:315-316 (2004).
Yamaori, S. et al., "Potent inhibition of human cytochrome P450 3A isoforms by cannabidiol: Role of phenolic hydroxyl groups in the resorcinol moiety," Life Sciences, 88:730-736 (2011).
Yu et al., "Reduced sodium current in GABAergic interneurons in a mouse model of severe myoclonic epilepsy in infancy," Nature Neuroscience, 9(9):1142-1149 (2006).
Yuriev, "Endogenic cannabinoid system is a new perspective object of pharmacotherapeutic effect to disease of nervous system," Ukrainsky Mnemotechny Chasopis, 6(50):21-29 (2005) (with English Abstract).
Zhao et al., "Chapter 27: Repetitive Seizures in the Immature Brain," Models of Seizures and E[epilepsy, 341-350 (2006).
Zhornitsky & Potvin, "Cannabidiol in Humans—The Quest for Therapeutic Targets," Pharmaceuticals, 5:529-552 (2012).
Zuardi et al., "Cannabidiol, a Cannabis sativa constituent, as an antipsychotic drug," Braz J Med Biol Res., 39(4):421-429 (2006).
Zuardi et al., "Cannabidiol: from an inactive cannabinoid to a drug with wide spectrum of action," Rev Bras Psiquiatr, 30(3):271-280 (2008).
U.S. Appl. No. 14/741,829, filed Jun. 17, 2015.
U.S. Appl. No. 15/519,244, filed Apr. 14, 2017.
U.S. Appl. No. 15/640,033, filed Jun. 30, 2017.
U.S. Appl. No. 16/314,569, filed Dec. 31, 2018.
U.S. Appl. No. 16/467,639, filed Jun. 7, 2019.
U.S. Appl. No. 16/486,750, filed Aug. 16, 2019.
U.S. Appl. No. 16/624,106, filed Dec. 18, 2019.
U.S. Appl. No. 16/737,707, filed Jan. 8, 2020.
U.S. Appl. No. 16/651,751, filed Mar. 27, 2020.
U.S. Appl. No. 16/764,701, filed May 15, 2020.
U.S. Appl. No. 16/768,241, filed May 29, 2020.
U.S. Appl. No. 16/893,018, filed Jun. 4, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 17/025,130, filed Sep. 18, 2020.
U.S. Appl. No. 17/050,956, filed Oct. 27, 2020.
U.S. Appl. No. 16/935,005, filed Jul. 21, 2020.
U.S. Appl. No. 17/296,066, filed May 21, 2021.
U.S. Appl. No. 17/296,076, filed May 21, 2021.
U.S. Appl. No. 17/340,885, filed Jun. 7, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/470,382, filed Sep. 9, 2021.
U.S. Appl. No. 17/472,000, filed Sep. 10, 2021.
U.S. Appl. No. 17/472,016, filed Sep. 10, 2021.
U.S. Appl. No. 17/477,172, filed Sep. 16, 2021.
U.S. Appl. No. 17/606,370, filed Oct. 25, 2021.
U.S. Appl. No. 17/611,824, filed Nov. 16, 2021.
U.S. Appl. No. 17/615,422, filed Nov. 30, 2021.
U.S. Appl. No. 17/552,487, filed Dec. 16, 2021.
U.S. Appl. No. 17/627,946, filed Jan. 18, 2022.
U.S. Appl. No. 17/631,069, filed Jan. 28, 2022.

METHODS OF TREATING TUBEROUS SCLEROSIS COMPLEX WITH CANNABIDIOL AND EVEROLIMUS

CROSS-REFERENCE TO RELATED APPLICATIONS

This application is a continuation of Ser. No. 17/188,766, filed Mar. 1, 2021, which claims the benefit of priority to U.S. Provisional Application No. 62/982,506, filed Feb. 27, 2020, and GB Provisional Application No. 2002754.6, filed Feb. 27, 2020, the entire contents of each of which are herein incorporated by reference in its entirety for all purposes.

BACKGROUND

Tuberous sclerosis complex (TSC) is a genetic disorder characterized by growth of distinctive benign tumors (hamartomas) and malformations (hamartias) in multiple organ systems. Tumors of the central nervous system (CNS) are the leading cause of morbidity and mortality in TSC patients, followed by renal disease. Patients with TSC can suffer from abnormalities of the brain that may include seizures, intellectual disability, and developmental delay, as well as abnormalities of the skin, lung, kidneys, and heart. The disorder affects as many as 25,000 to 40,000 individuals in the United States and about 1 to 2 million individuals worldwide, with an estimated prevalence of one in 6,000 newborns.

Inherited defects or de novo mutations associated with TSC occur on one of two genes, TSC1 and TSC2. Only one of the genes needs to be affected for TSC to be present. The TSC1 gene, on chromosome 9, produces a protein called hamartin. The TSC2 gene, discovered in 1993, is on chromosome 16 and produces the protein tuberin. Scientists believe these proteins act in a complex as growth suppressors by inhibiting the activation of a master, evolutionarily conserved kinase called mTOR. Loss of regulation of mTOR occurs in cells lacking either hamartin or tuberin, and this leads to abnormal differentiation and development, and to the generation of enlarged cells, as are seen in TSC brain lesions.

Between one fourth and one half of all children with TSC develop autism spectrum disorders (ASD). Almost all patients with TSC also develop epilepsy and most develop multiple seizure types. Furthermore, most patients with TSC have refractory epilepsy, and therefore are resistant to treatment with one or more anti-epileptic drugs. On average, TSC patients are resistant to five AED Presently, there is no monotherapy that can treat all conditions and symptoms associated with TSC. In order to treat tumors and epileptic seizures, TSC patients are commonly administered combinations of the drugs, such as an mTor inhibitor (e.g., everolimus) and an antiepileptic drug. In addition to TSC being generally refractory to multiple antiepileptic drugs, antiepileptic drugs can also have an adverse drug-drug interaction ("DDI") with everolimus. Thus, there exists a need for a safe and effective method of treating patients with everolimus and an antiepileptic drug.

SUMMARY

Applicant has discovered a method of safely and effectively treating TSC patients with cannabidiol ("CBD") and everolimus.

In some embodiments, the disclosure provides a method of treating TSC in a patient in need thereof, comprising administering everolimus in combination with a reduced dose of CBD.

In some embodiments, the patient is administered from about 2 mg to about 10 mg of everolimus. In some embodiments, the patient is administered about 2.5 mg, about 5 mg, or about 10 mg of everolimus. In some embodiments, the patient is administered 2.5 mg or 5 mg of everolimus. In some embodiments, the patient is administered 2.5 mg of everolimus. In some embodiments, the patient is administered 5 mg of everolimus.

In some embodiments, the reduced dose of CBD is at least about 10% less than the dose of CBD the patient would otherwise receive in the absence of everolimus. In some embodiments, the reduced dose of CBD is between 10% to 90% less than the dose of CBD the patient would otherwise receive in the absence of everolimus. In some embodiments, the reduced dose of CBD ranges from about 5 mg/kg/day to about 20 mg/kg/day. In some embodiments, the reduced dose of CBD is about 5 mg/kg/day, about 7 mg/kg/day, about 9 mg/kg/day, about 10 mg/kg/day, about 12 mg/kg/day, about 14 mg/kg/day, about 15 mg/kg/day, about 16 mg/kg/day, about 18 mg/kg/day, or about 20 mg/kg/day. In some embodiments, the reduced dose of CBD is about 5 mg/kg/day, about 10 mg/kg/day, about 15 mg/kg/day, or about 20 mg/kg/day. In some embodiments, the reduced dose of CBD is about 5 mg/kg/day. In some embodiments, the reduced dose of CBD is about 10 mg/kg/day. In some embodiments, the reduced dose of CBD is about 15 mg/kg/day. In some embodiments, the reduced dose of CBD is about 20 mg/kg/day.

In some embodiments, the patient is administered 2.5 mg of everolimus, and a reduced dose of CBD selected from the group consisting of about 5 mg/kg/day, about 10 mg/kg/day, about 15 mg/kg/day, and about 20 mg/kg/day. In some embodiments, the patient is administered 2.5 mg of everolimus, and the reduced dose of CBD is selected from the group consisting of about 10 mg/kg/day, about 15 mg/kg/day, and about 20 mg/kg/day. In some embodiments, the patient is administered 2.5 mg of everolimus, and the reduced dose of CBD is about 20 mg/kg/day. In some embodiments, the patient is administered 5 mg of everolimus, and a reduced dose of CBD selected from the group consisting of about 5 mg/kg/day, about 10 mg/kg/day, about 15 mg/kg/day, and about 20 mg/kg/day. In some embodiments, the patient is administered 5 mg of everolimus, and the reduced dose of CBD selected from the group consisting of about 10 mg/kg/day, about 15 mg/kg/day, and about 20 mg/kg/day. In some embodiments, the patient is administered 5 mg of everolimus, and the reduced dose of CBD is about 20 mg/kg/day.

In some embodiments, the CBD is present in a highly purified botanical drug substance. In some embodiments, the CBD has a purity of at least 95% w/w. In some embodiments, the CBD has a purity of at least 98% w/w. In some embodiments, wherein the CBD is synthetic CBD.

In some embodiments, the disclosure provides for methods of treating seizures associated with tuberous sclerosis complex in an everolimus-naive patient, wherein the patient is currently treated with CBD, comprising: (a) administering everolimus to the patient; (b) monitoring the patient's blood plasma levels of everolimus; and (c) if the patient's blood plasma trough concentrations of everolimus exceed 15 ng/mL, then reducing the dose of everolimus by at least 10%. In some embodiments, the patient is treated with 25 mg/kg/day CBD. In some embodiments, step (a) comprises administering 5 mg/m² everolimus once daily. In some embodiments, step (a) comprises administering a starting dose of everolimus of 5 mg/m² everolimus once daily, and titrating up the everolimus dose by no more than 5 mg (e.g., 1, 2, 3, 4, or 5 mg). In some embodiments, the dose of everolimus is titrated every 1 to 2 weeks until the patient's blood plasma trough concentration of everolimus is within the range of 5-15 ng/mL. In some embodiments, the monitoring in step (b) occurs 1 to 2 weeks after the patients begins administering everolimus. In some embodiments, the dose of everolimus is reduced to provide blood plasma trough concentration of everolimus is within the range of 5-15 ng/mL. In some embodiments, the dose of everlimus is reduced (e.g., by about 10%, about 15%, about 20%, about 25%, about 30%, about 35%, about 40%, about 45%, or about 50%) to provide a Cmax that is not more than about 45 ng/mL, about 40 ng/mL, about 35 ng/mL, about 30 ng/mL, about 25 ng/mL or about 20 ng/mL. In some embodiments, the dose of everlimus is reduced to provide an $AUC_{0-24}$ that is not more than about 490 h*ng/mL, about 450 h*ng/mL, about 400 ng/mL, about 350 h*ng/mL, about 300 h*ng/mL, about 250 h*ng/mL, or about 200 h*ng/mL.

In some embodiments, the disclosure provides for methods of treating seizures associated with tuberous sclerosis complex in an everolimus-naive patient, wherein the patient is currently treated with CBD, comprising: (a) administering everolimus to the patient; (b) monitoring the patient's blood plasma levels of everolimus; and (c) if the patient's Cmax exceeds 50 ng/mL or $AUC_{0-last}$ 500 h*ng/mL, then reducing the dose of everolimus by at least 10%. In some embodiments, the patient is treated with 25 mg/kg/day CBD. In some embodiments, step (a) comprises administering 5 mg/m² everolimus once daily. In some embodiments, step (a) comprises administering a starting dose of everolimus of 5 mg/m² everolimus once daily, and titrating up the everolimus dose by no more than 5 mg (e.g., 1, 2, 3, 4, or 5 mg). In some embodiments, the dose of everolimus is titrated every 1 to 2 weeks until the patient's blood plasma trough concentration of everolimus is within the range of 5-15 ng/mL. In some embodiments, the monitoring in step (b) occurs 1 to 2 weeks after the patients begins administering everolimus. In some embodiments, the dose of everolimus is reduced to provide blood plasma trough concentration of everolimus is within the range of 5-15 ng/mL. In some embodiments, the dose of everlimus is reduced (e.g., by about 10%, about 15%, about 20%, about 25%, about 30%, about 35%, about 40%, about 45%, or about 50%) to provide a Cmax that is not more than about 45 ng/mL, about 40 ng/mL, about 35 ng/mL, about 30 ng/mL, about 25 ng/mL or about 20 ng/mL. In some embodiments, the dose of everlimus is reduced to provide an $AUC_{0-24}$ that is not more than about 490 h*ng/mL, about 450 h*ng/mL, about 400 ng/mL, about 350 h*ng/mL, about 300 h*ng/mL, about 250 h*ng/mL, or about 200 h*ng/mL.

In some embodiments, the seizures are focal seizures. In some embodiments, the focal seizures are focal motor seizures without impairment of consciousness or awareness; focal seizures with impairment of consciousness or awareness; or focal seizures evolving to bilateral generalized convulsive seizures and generalized seizures. In some embodiments, the generalized seizures are tonic-clonic, tonic, clonic or atonic seizures. In some embodiments, the seizures are generalized seizures. In some embodiments, the generalized seizures are tonic-clonic, tonic, clonic or atonic seizures. In some embodiments, the total number of seizures are reduced by 10%, 20%, 30%, 40%, 50%, 60%, 70%, 80%, 90%, or 100% compared to baseline. In some embodiments, the total number of seizures are reduced by at least 50% compared to baseline. In some embodiments, the total number of focal seizures are reduced by at least 50% compared to baseline. In some embodiments, the focal seizures are focal motor seizures without impairment of consciousness or awareness; focal seizures with impairment of consciousness or awareness; or focal seizures evolving to bilateral generalized convulsive seizures and generalized seizures. In some embodiments, the total number of tonic-clonic, tonic, clonic, atonic or absence seizures are reduced by at least 50% compared to baseline.

In some embodiments, the disclosure provides a method of treating seizures associated with tuberous sclerosis complex in a patient in need thereof, comprising administering from 2.5-10 mg of everolimus in combination with cannabidiol (CBD), wherein the CBD has a purity of at least 95% w/w, and the CBD is administered at a dose ranging from about 10 mg/kg/day to about 20 mg/kg/day. In some embodiments, the patient is administered about 2.5 mg, about 5 mg, or about 10 mg of everolimus. In some embodiments, the patient is administered 2.5 mg or 5 mg of everolimus. In some embodiments, the dose of CBD is about 10 mg/kg/day, about 15 mg/kg/day, or about 20 mg/kg/day. In some embodiments, the dose of CBD is about 20 mg/kg/day. In some embodiments, the seizures are focal seizures. In some embodiments, the focal seizures are focal motor seizures without impairment of consciousness or awareness; focal seizures with impairment of consciousness or awareness; or focal seizures evolving to bilateral generalized convulsive seizures and generalized seizures. In some embodiments, the generalized seizures are tonic-clonic, tonic, clonic or atonic seizures. In some embodiments, the seizures are generalized seizures. In some embodiments, the generalized seizures are tonic-clonic, tonic, clonic or atonic seizures. In some embodiments, the total number of seizures are reduced by 10%, 20%, 30%, 40%, 50%, 60%, 70%, 80%, 90%, or 100% compared to baseline. In some embodiments, the total number of seizures are reduced by at least 50% compared to baseline. In some embodiments, the total number of focal seizures are reduced by at least 50% compared to baseline. In some embodiments, the focal seizures are focal motor seizures without impairment of consciousness or awareness; focal seizures with impairment of consciousness or awareness; or focal seizures evolving to bilateral generalized convulsive seizures and generalized seizures. In some embodiments, the total number of tonic-clonic, tonic, clonic, atonic or absence seizures are reduced by at least 50% compared to baseline.

DETAILED DESCRIPTION

Definitions

Figure 1:
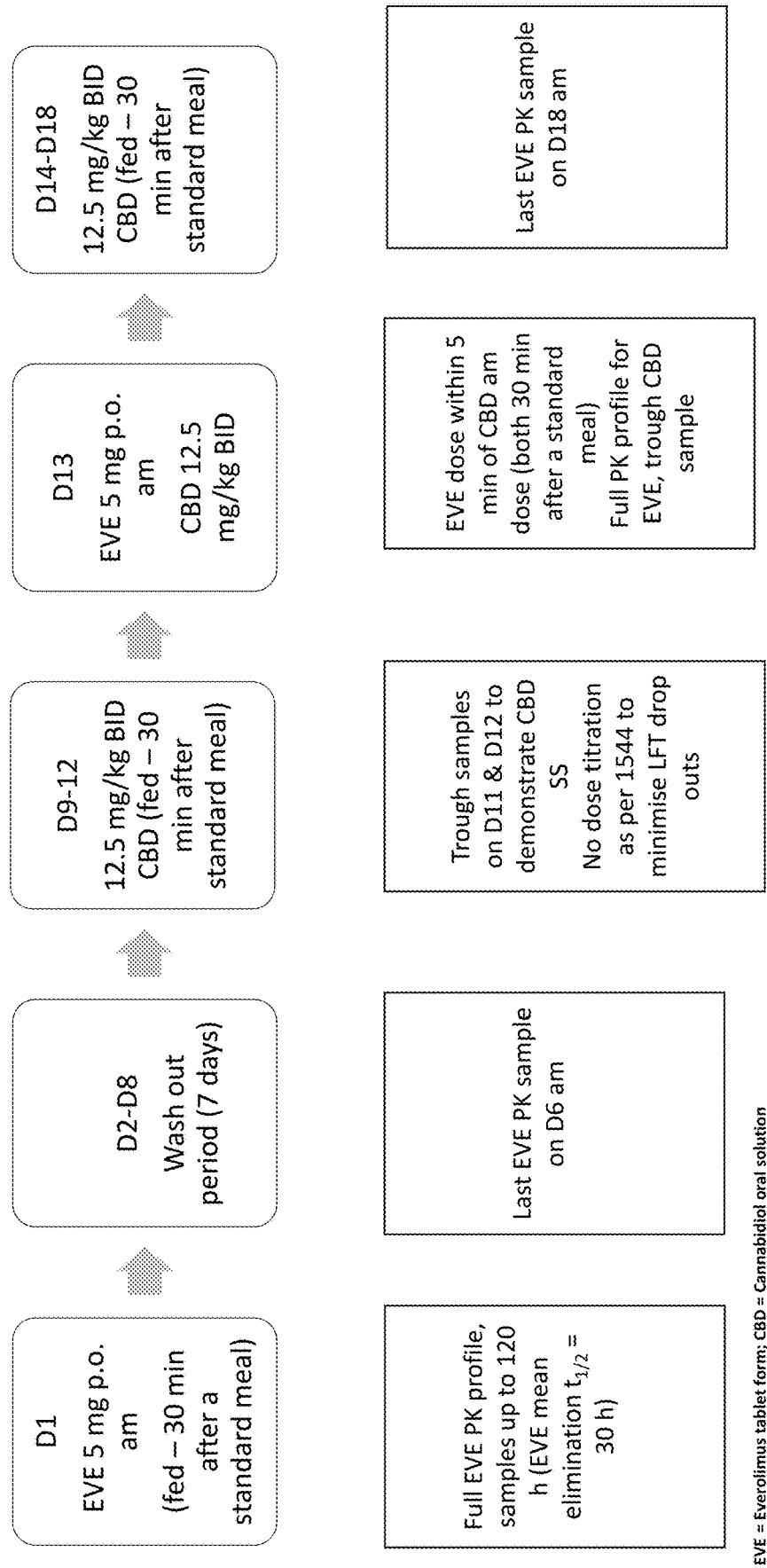
FIG. 1 schematically illustrates that trial design to measure the impact of everolimus (5 mg daily dose) on the pharmacokinetics of CBD (25 mg/kg/day).

As used herein, the term "about" refers to an acceptable degree of variation in the art. In some embodiments, "about" means plus or minus 10% of the referenced number unless otherwise stated or otherwise evident by the context, and except where such a range would exceed 100% of a possible value, or fall below 0% of a possible value, such as less than 0% content of an ingredient, or more than 100% of the total contents of a composition.

The term "a" or "an" refers to one or more of that entity; for example, "an antiepileptic drug" (AED) refers to one or more AED or at least one AED. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

In some embodiments, the compositions contain cannabidiol ("CBD"). As used herein, CBD refers to synthetic CBD or to a *Cannabis* extract, which contains between 95% w/w to 100% w/w CBD. In some embodiments, the CBD extract can contain between about 95% w/w, about 96% w/w, about 97% w/w, about 98% w/w, about 99% w/w, or about 100% w/w. In some embodiments, the CBD extract contains 98% w/w CBD. Such a *Cannabis* extract, containing at least 95% w/w CBD, may be referred to as a highly pure botanical drug substance. In some embodiments, the CBD extract contains about 99% w/w CBD. Unless otherwise noted, references to CBD in the present disclosure should be understood as references to the decarboxylated version of the CBD, and do not include the acidic CBDA.

As used herein, "purity" and "pure" when modifying CBD refers to the weight of CBD in the drug substance based on the total weight of all cannabinoids in the drug substance. Additional cannabinoids that may be present in the drug substance include, without limitation, CBDV, $\Delta$9THC, and CBD-C4, and combinations thereof. For avoidance of doubt, drug substance is distinct from a drug product. Drug product refers to the pharmaceutical composition containing the drug substance. Accordingly, when the present disclosure refers to administering CBD which has a purity of at least 95% w/w (or similar expressions), the purity refers to CBD in the drug substance, not the drug product.

As defined herein, a "reduced dose" of CBD is less than the dose that an otherwise identical patient with TSC would receive if said patient were not coadministered everolimus. In other words, the reduced dose of CBD administered to a patient with TSC in combination with everolimus is less than the dose of CBD administered to the same (or similar) TSC patient in the absence of everolimus. The dose of CBD that the patient would otherwise receive in the absence of everolimus (i.e., if the patient was not coadministered everolimus) may be referred to as the "reference dose" or the "recommended dose" of CBD. "Reference dose" or "recommended dose" may be used interchangeably. Furthermore, "reference dose" and "recommended dose" are distinct from a "starting dose." A "starting dose" is the dose administered to the patient to initiate treatment. The "starting dose" is a lower dose than the "reference dose" and is administered for a period of time (e.g., over the course of 1 week) before the patient increases the dose to the "reference dose".

In some embodiments, the "reference dose" or "recommended dose" of CBD ranges from about 10 mg/kg/day, to about 50 mg/kg/day. In some embodiments, the "reference dose" of CBD is the dose that is approved (e.g., by the FDA or the EMA) for treating seizures in the particular patient. For nearly all FDA approved drugs, the "recommended" dose (or doses) of the drug are determined based on the plasma level (or range of plasma levels) of the drug required to provide the desired clinical effect(s) and/or avoid undesirable side effects. The recommended dose(s) of a particular drug are those recognized in the art as suitable for treating a patient with particular physical characteristics (or within a range of particular characteristics), and are thus the dose(s) provided in the package insert for the drug. There may be multiple recommended doses for a particular condition. For example, there are two recommended doses of EPIDIOLEX® (November 2018; revised July 2020) for treating seizures associated with Lennox-Gastaut or Dravet Syndrome—(1) a maintenance dosage of 10 mg/kg/day and (2) a maximum recommended maintenance dosage of 20 mg/kg/day. For avoidance of doubt, both doses (i.e. (1) and (2)) are considered a "recommended dose" according to this disclosure. Thus, in various embodiments, the methods of the present disclosure are directed to adjustments or changes in the dosing of CBD relative to the FDA "recommended" dose, e.g., in the package insert for CBD, as suitable for treating a TSC patient with particular physical characteristics. The particular characteristics may include hepatic impairment, since patients with moderate or severe hepatic impairment receive different recommended doses of CBD as described herein and according to the EPIDIOLEX® drug label (November 2018; revised July 2020). Thus, as used herein, the "reference dose" or "recommended dose" for CBD is distinct from doses which may be disclosed by particular physicians for particular patients. Depending on the specific pharmacokinetics and pharmacodynamics of the drug, the recommended dose may vary depending on one or more physical and physiological characteristics of the patient, for example age, gender, weight, body mass index, liver metabolic enzyme status (e.g., poor or extensive metabolizer status), disease state, etc.

At the time of this disclosure, Applicant contemplates that the approved dosing of CBD (in the absence of everolimus) for TSC ranges from 5 mg/kg/day to 25 mg/kg/day (e.g., for patients with normal hepatic status or mild hepatic impairment). Applicant contemplates that TSC patients will receive a starting dose of 5 mg/kg/day of CBD, and the starting dose may be increased to achieve and/or maintain efficacy. Typically, efficacious doses may be 10 mg/kg/day, about 15 mg/kg/day, about 20 mg/kg/day, or about 25 mg/kg/day when administered in the absence of everolimus, although the exact efficacious dose will depend on the specific patient and the patient's physical and physiological characteristics. Therefore, in some embodiments, the "reference dose" of CBD is about 10 mg/kg/day, about 15 mg/kg/day, about 20 mg/kg/day, or about 25 mg/kg/day. In July of 2020 (after the priority date of the present application), the FDA approved CBD for treating seizures associated with TSC. According to the drug label for EPIDIOLEX® (revised July 2020), the recommended dosage for treating seizures associated with is 25 mg/kg/day (e.g., for patients with normal hepatic status or mild hepatic impairment). Thus, in some embodiments, the reduced dose is less than the 25 mg/kg/day reference dose of EPIDIOLEX® that is approved for treating seizures associated TSC according to the drug label for EPIDIOLEX® (revised July 2020).

In some embodiments, the methods of the present disclosure provide for reducing the dose of CBD that the patient would otherwise receive in the absence of everolimus. For example, if a TSC patient is administered 10 mg/kg/day of CBD in the absence of everolimus, when coadministered everolimus the TSC patient will receive less than 10 mg/kg/day as a reduced dose (e.g. about 1 mg/kg/day, about 2 mg/kg/day, about 3 mg/kg/day, about 4 mg/kg/day, about 5 mg/kg/day, about 6 mg/kg/day, about 7 mg/kg/day, about 8 mg/kg/day, or about 9 mg/kg/day). For example, if a TSC patient is administered 15 mg/kg/day of CBD in the absence of everolimus, when coadministered everolimus the TSC patient will receive less than 15 mg/kg/day as a reduced dose (e.g. e.g. about 1 mg/kg/day, about 2 mg/kg/day, about 3 mg/kg/day, about 4 mg/kg/day, about 5 mg/kg/day, about 6 mg/kg/day, about 7 mg/kg/day, about 8 mg/kg/day, about 9 mg/kg/day, about 10 mg/kg/day, about 11 mg/kg/day, about 12 mg/kg/day, about 13 mg/kg/day, or about 14 mg/kg/day). As another example, if a TSC patient is administered 20 mg/kg/day of CBD in the absence of everolimus, when coadministered everolimus the TSC patient will receive less than 20 mg/kg/day as a reduced dose (e.g. about 1 mg/kg/day, about 2 mg/kg/day, about 3 mg/kg/day, about 4 mg/kg/day, about 5 mg/kg/day, about 6 mg/kg/day, about 7 mg/kg/day, about 8 mg/kg/day, about 9 mg/kg/day, about 10 mg/kg/day, about 11 mg/kg/day, about 12 mg/kg/day, about 13 mg/kg/day, about 14 mg/kg/day, about 15 mg/kg/day, about 16 mg/kg/day, about 17 mg/kg/day, about 18 mg/kg/day, about 19 mg/kg/day). As yet another example, if a TSC patient is administered 25 mg/kg/day of CBD in the absence of everolimus, when coadministered everolimus the TSC patient will receive less than 25 mg/kg/day as a reduced dose (e.g. about 1 mg/kg/day, about 2 mg/kg/day, about 3 mg/kg/day, about 4 mg/kg/day, about 5 mg/kg/day, about 6 mg/kg/day, about 7 mg/kg/day, about 8 mg/kg/day, about 9 mg/kg/day, about 10 mg/kg/day, about 11 mg/kg/day, about 12 mg/kg/day, about 13 mg/kg/day, about 14 mg/kg/day, about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, or about 24 mg/kg/day). As used herein, the amounts of CBD in mg/kg/day or in mg/kg refer to the amount of drug substance (i.e., CBD) that is administered regardless of the purity of CBD in the drug substance.

As used herein, "treat" or "treating" means one or more of relieving, alleviating, delaying, reducing, reversing, improving, or managing at least one symptom of a condition in a subject. Such symptoms may include, without limitation, the onset, frequency, or duration of one or more types of seizures. Seizures associated with TSC include, without limitation, infantile seizures, focal seizures (with or without impairment or consciousness or awareness; focal seizures evolving to bilaterial generalized convulsive seizures and generalized seizures) tonic seizures, clonic seizures, tonic-clonic seizures, atonic seizures, myoclonic seizures, and absence seizures. The term "treating" may also mean one or more of arresting, delaying the onset (i.e., the period prior to clinical manifestation of the condition) or reducing the risk of developing or worsening a condition.

As used herein, the term an "otherwise identical patient" or an "otherwise identical patient who is not coadministered everolimus" refers to a patient whose physical characteristics relevant to drug (e.g., CBD) dosing are expected to be substantially the same as that of the patient being treated with a reduced CBD dose according to the presently disclosed methods—except that the patient is not concomitantly administered everolimus. In some embodiments, the otherwise identical patient will be of substantially the same age, sex, and body weight. In some embodiments, the substantially identical patient will also have substantially identical hepatic function and drug metabolism.

As used herein, the term "coadministered" means that one or more drugs are administered on the same day. In some embodiments, the one or more drugs (e.g. cannabidiol and everolimus) are administered sequentially. In some embodiments, the one or more drugs (e.g. cannabidiol and everolimus) are administered simultaneously.

As used herein, "hepatic impairment" means a reduction in normal liver executory and metabolic function compared to an otherwise healthy liver. The liver is involved in the clearance of many drugs through a variety of oxidative and conjugative metabolic pathways and/or through biliary excretion of unchanged drug or metabolites. Alterations of these excretory and metabolic activities by hepatic impairment can lead to drug accumulation or, less often, failure to form an active metabolite. In some embodiments, hepatic impairment can be determined using the Child Pugh score. The Child Pugh score is described in Cholongitas, et al. "Systematic review: The model for end-stage liver disease—should it replace Child-Pugh's classification for assessing prognosis in cirrhosis?". *Alimentary Pharmacology & Therapeutics.* 22 (11-22): 1079-89, which is herein incorporated by reference in its entirety.

The Child Pugh score employs five clinical measures of liver disease. Each measure is scored 1-3, with 3 indicating most severe derangement. Either the prothrombin time or INR should be used to calculate the Child-Pugh score, not both.

| Measure | 1 point | 2 points | 3 points |
| --- | --- | --- | --- |
| Total bilirubin, (mg/dL) | (<2) | (2-3) | (>3) |
| Serum albumin, g/dL | >3.5 | 2.8-3.5 | <2.8 |
| Prothrombin time, prolongation (s) | <4.0 | 4.0-6.0 | >6.0 |
| INR | <1.7 | 1.7-2.3 | >2.3 |
| Ascites | None | Mild (or suppressed with medication) | Moderate to severe (or refractory) |
| Hepatic encephalopathy | None | Grade I-II | Grade III-IV |

Chronic liver disease is classified into Child-Pugh class A to C, employing the added score from above.

| Points | Class |
| --- | --- |
| 5-6 | A |
| 7-9 | B |
| 10-15 | C |

In some embodiments, a patient with "mild hepatic impairment" has a Child Pugh score of A. In some embodiments, a patient with "moderate hepatic impairment" has a Child Pugh score of B. In some embodiments, a patient with "severe hepatic impairment" has a Child Pugh score of C.

In some embodiments, "mild hepatic impairment" is bilirubin≤1×the upper limit of the normal range ("ULN") and aspartate aminotransferase ("AST")>1×ULN, or bilirubin>1.0-1.5×ULN and any amount of AST above ULN is present. In some embodiments, "moderate hepatic impairment" is bilirubin>1.5-3.033×ULN and any amount of AST above ULN is present. In some embodiments, "severe hepatic impairment" is bilirubin≥3.0×ULN and any amount of AST above ULN is present. In some embodiments, serum transaminases (ALT and AST) and total bilirubin levels are obtained prior to starting treatment.

Methods of Treating TSC Using CBD and Everolimus

Patients with TSC have treatment-resistant epilepsy. This form of epilepsy is associated with several seizure types including, without limitation, infantile seizures, focal seizures (with or without impairment or consciousness or awareness; focal seizures evolving to bilateral generalized convulsive seizures and generalized seizures) tonic seizures, clonic seizures, tonic-clonic seizures, atonic seizures, myoclonic seizures, and absence seizures, tonic seizures, myoclonic seizures, and absence seizures. Patients with TSC also exhibit noncancerous growths in many parts of the body, including the brain, skin, kidneys, and other organs. The present disclosure provides methods of treating seizures in patients diagnosed with TSC, comprising administering everolimus in combination with a reduced dose of CBD.

CBD (under the brandname EPIDIOLEX®) is approved by the Food and Drug Administration (FDA) for the treatment of Lennox-Gastaut syndrome and Dravet Syndrome at doses ranging from 5 mg/kg/day to 20 mg/kg/day. Everolimus is approved by the FDA for the treatment of patients with TSC that have subependymal giant cell astrocytoma (SEGA) at a dose of 4.5 mg/m$^2$ once daily, for TSC-associated renal angiomyolipoma at a dose of 10 mg orally once daily, and as an adjunctive treatment for TSC-associated partial-onset seizures at a dose of 5 mg/m$^2$ once daily.

Because TSC patients also experience seizures described herein, Applicant discovered that CBD can be used in combination with everolimus to treat TSC patients. Indeed, in July of 2020, after the priority date of the present application, the FDA approved CBD for treating seizures associated with TSC. According to the drug label for EPIDIOLEX® (revised July 2020), the recommended dosage for treating seizures associated with is 25 mg/kg/day (e.g., for patients with normal hepatic status or mild hepatic impairment). However, Applicant discovered a potentially serious adverse drug-drug interaction ("DDI") between CBD and everolimus. Applicant found that reducing the dose of everolimus (e.g., as prescribed in the everolimus package insert or drug label) is not sufficient to address the DDI between CBD and everolimus. In some embodiments, Applicant surprisingly and unexpectedly found that the reference dose of CBD must be reduced to safely treat TSC patients that are concurrently treated with everolimus, and the reduced dose is also efficacious. In some embodiments, Applicant surprisingly and unexpectedly found that reducing the dose of both CBD and everolimus is critical to safely and effectively coadminister CBD and everolimus in order to treat TSC.

The most common types of DDIs involve the inhibition or induction of one or more drug-metabolizing enzymes by a drug. When inhibitors or inducers of a particular drug-metabolizing enzyme are coadministered with a drug that is metabolized by that enzyme (known as a substrate of that enzyme), the pharmacokinetic parameters of one or both drugs change, leading to increased or decreased drug exposures. It is this change in exposure that may result in adverse events. However, an increase in pharmacokinetic parameters, alone, does not necessarily produce an adverse event, and require a dose modification. Only if the increase in the pharmacokinetic parameters presents a risk to the patient is a dose modification required. However, dosing modifications are unpredictable. Reducing a dose too much risks undertreating the patients, but over-dosing (e.g. not reducing the dose, or not reducing the dose enough) can increases exposure to potentially dangerous levels.

A drug of interest is classified as a weak, moderate, or strong CYP3A inhibitor based on the effect of the drug of interest on the plasma area under-the-curve (AUC) of the prototypical CYP3A4/CYP3A5 substrate midazolam. If a drug of interest increases the AUC of midazolam≥5 fold, the drug of interest is a strong CYP3A inhibitor. If the drug of interest increases the AUC of midazolam increases >2.0 to 4.9 fold, the drug of interest is a moderate CYP3A inhibitor. If the drug of interest increases the AUC of midazolam≤2 fold, the drug of interest is a weak CYP3A inhibitor.

According to the FDA-approved drug label (also referred to as the Prescribing Information) for everolimus (AFINITOR® and AFINITOR DISPERZ®, updated January 2019, herein incorporated by reference in its entirety), everolimus is a substrate for P-gp and CYP3A4. Everolimus is also reported to be a substrate for CYP3A5, and CYP2C8.

Combined P-pg and CYP3A4 inhibitors are known to increase everolimus exposure. For example, ketoconazole, a P-gp and strong CYP3A4 inhibitor, increases the $C_{max}$ and AUC of everolimus by 3.9 and 15-fold, respectively. Erythromycin, a P-gp and moderate CYP3A4 inhibitor increases the $C_{max}$ and AUC of everolimus by 2.0 and 4.4-fold, respectively. Verapamil, a P-gp and moderate CYP3A4 inhibitor, increases the $C_{max}$ and AUC of everolimus by 2.3 and 3.5-fold, respectively.

The FDA label of everolimus contraindicates concomitant administration of everolimus and a P-gp and strong CYP3A4 inhibitors. With respect to P-gp and moderate CYP3A4 inhibitors, the everolimus label instructs that the dose of everolimus is reduced. Specifically, for patients with TSC-associated renal angiomyolipoma, the label instructs patients to reduce the dose of everolimus to 2.5 mg once daily. The label also provides instructions to increase the dose to 5 mg if it can be tolerated. Three days after discontinuing the P-gp and moderate CYP3A4 inhibitor, patients can resume treatment with the everolimus dose that was administered prior to inhibitor use. In patents with TSC-associated SEGA and TSC-associated partial-onset seizures, the label instructs patients to reduce the daily dose (as described herein and on the FDA label) by 50%. If the reduced dose is lower than the lowest available strength of everolimus, patients should change to dosing every other day. Three days after discontinuing the P-gp and moderate CYP3A4 inhibitor, patients can resume treatment with the everolimus dose that was administered prior to inhibitor use.

The label also indicates that everolimus shows low levels of CYP3A4 of CYP2D6 inhibition, but the interaction was deemed "not clinically significant." (Section 12.3 of the AFINITOR/AFINITOR DISPERZ Label). Specifically, coadministration of an oral dose of midazolam (sensitive CYP3A4 substrate) with AFINITOR resulted in a 25% increase in midazolam Cmax and a 30% increase in midazolam $AUC_{0-inf}$. Similarly, co-administration of everolimus with other CYP3A4 substrates, including atorvastatin, pravastatin, and simvastatin, did not produce pharmacodynamic result and was demeaned not clinically relevant. Thus, prior to the present disclosure, everolimus was not expected cause clinically significant drug-drug interactions through CYP3A4 of CYP2D6 inhibition. Accordingly, there was no expectation that the dosage of a drug coadminstered with everolimus, such as CBD, should be reduced in order to safely treat TSC patients.

The pharmacological properties of CBD are not fully elucidated. As indicated on the FDA approved label for EPIDIOLEX®, CBD is metabolized in the liver and the gut, and is a substrate CYP2C19 and CYP3A4 enzymes and UGT1A7, UGT1A9, and UGT2B7 isoforms. CBD inhibits uridine 5'-diphospho-glucuronosyltransferase (UGT) enzymes UGT1A9 and UGT2B7. CBD is reported to be an inhibitor of CYP2B6, CYP2C8, CYP2C9, and CYP2C19. Data also suggest that CBD has the potential to inhibit CYP3A4, but the strength or clinical significance of this interaction is unknown. CBD also has the potential to induce or inhibit CYP1A2 and CYP2B6 at clinically relevant concentrations, but the strength or clinical significance of this interaction is unknown. Thus, it is not known if CBD is a strong, moderate, or weak inhibitor of any CYP isoform, or indeed if CBD-mediated inhibition of any of any of these enzymes produces a clinically significant result. Lastly, Applicant discovered that a metabolite of CBD, 7-COOH-CBD is a substrate for P-gp. 7-COOH-CBD is an inhibitor of transport mediated via BCRP and BSEP at clinically relevant concentrations.

Applicant discovered that elevated levels of CBD cause transaminase elevation, rash, somnolence, sedation, lethargy, diarrhea, pyrexia, weight decreased, nasopharyngitis, irritability, oropharyngeal pain, and decreased appetite. Transaminase can lead to hepatic dysfunction, including unexplained nausea, vomiting, right upper quadrant abdominal pain, fatigue, anorexia, or jaundice and/or dark urine. Elevated exposure of everolimus exposure is known to cause non-infectious pneumonitis, infections, severe hypersensitivity to reactions, angioedema, stomatitis, renal failure, impaired wound healing, metabolic disorders, myelosuppression, risk of infection or reduced immune response with vaccination, embryo-fetal toxicity, and *stomatis*, respiratory tract infection. The methods of the disclosure reduce the incidence of one or more of the above side effects.

Applicant found that when CBD is administered at a steady state orally in combination with midazolam, CBD exerts no clinically significant effect on midazolam's pharmacokinetic parameters (See Example 2). In other words, the DDI with midazolam (if any) predicts that CBD is a weak inhibitor of CYP3A4. Therefore, CBD should have no clinically relevant impact on everolimus (a CYP3A4 substrate drug). Similarly, DDI studies for everolimus described herein predict that everolimus should have no clinically relevant impact on CBD. However, Applicant unexpectedly found that a potentially clinically significant DDI occurs when everolimus and CBD are co-administered. Without being bound by theory, the DDI that the Applicant observed may result from a previously unknown mechanism whereby CBD inhibits P-gp-mediated efflux of everolimus. The everolimus label contains no instructions to adjust the dose when administered with a P-gp inhibitor that is not also a moderate or strong CYP3A4 inhibitor. Additionally or alternatively, combined CYP3A4 inhibition by both CBD and everolimus may be significant enough to produce a new and unexpected pharmacodynamic effect.

Prior to Applicant's invention, it was believed that administering everolimus according to the instructions on the FDA-approved label was sufficient to address DDI. Because the everolimus label contains no instructions to adjust the dose when administered with a P-gp inhibitor that is not a moderate or strong CYP3A4 inhibitor, a skilled artisan would have believed that no dose reduction was required with treating a patient with both CBD and everolimus. For combined P-gp and moderate CYP3A4 inhibitors (which CBD is not), the everolimus label instructions patients to reduce the dose of everolimus from 10 mg, to a dose of 5 mg and then 2.5 mg. However, Applicant was surprised to discover that for patients already treated with everolimus at the time of initiating CBD treatment, the adjustment is not sufficient, and the clinically significant interaction persisted. The dose of everolimus could not be reduced further without sacrificing the clinical efficacy of everolimus.

In some embodiments, Applicant found that, in addition to dose reductions of everolimus, a dose reduction of CBD is required to safely and effectively treat seizures in TSC patients. In some embodiments, the reduced doses of CBD and everolimus that are effective when coadministered, are ineffective when CBD and everolimus are not coadministered (e.g. when the reduced dose of CBD is administered without everolimus or when everolimus is administered without CBD). In some embodiments, the reduced doses of CBD is less than the approved dose for TSC, but falls within levels approved for treating seizures associated with other forms of epilepsy (e.g., Lennox-Gastaut syndrome and Dravet syndrome).

For purposes of this disclosure, "reduced dose" may be referred to alternatively as a dose reduction, down dose, downward dose, or downward titration. For example, in some embodiments, the recommended dose of CBD for treating seizures with TSC is 25 mg/kg/day CBD. If the patient is coadminstered everolimus, the patient may downward titrate CBD to 20 mg/kg/day, 15 mg/kg/day, or 10 mg/kg/day. Similarly, a dose reduction, down dose or downward dose of CBD may required, desired, or considered to safely and effectively treat seizures associated with TSC.

In some embodiments, the disclosure provides for methods of treating seizures associated with TSC in a everolimus-naive patient, wherein the patient is currently treated with CBD, and the patient is in need of treatment with everolimus. As used herein, an "everolimus-naive patient" refers to a patient that is not currently being treated with everolimus. Rather, the everolimus-naive patient is currently treated with CBD to reduce seizures, and the patient is in need of everolimus. The term "everolimus naive patient" encompasses patients that may have been treated with everolimus previously, provided that they are not being treated with everolimus when receiving CBD treatment. In some embodiments, the method comprises monitoring the patient's blood plasma levels of everolimus, and reducing the dose of everolimus (e.g., by 5%, 10%, 15%, 20%, 25%, 30%, 35%, 40%, 45%, or 50%) when everolimus trough plasma levels exceed 15 ng/mL, when Cmax(ss) is greater than or equal to about 46 ng/mL, about 40 ng/mL, about 35 ng/mL, about 30 ng/mL, about 25 ng/mL, or about 20 ng/mL (including all values and ranges therebetween), and/or when AUC(ss) is greater than or equal to about 530 h*ng/mL, about 500 h*ng/mL, about 450 h*ng/mL, about 400 h*ng/mL, about 350 h*ng/mL, about 300 h*ng/mL, about 250 h*ng/mL, or about 200 h*ng/mL (including all values and ranges therebetween).

Cannabidiol (CBD)

CBD has the following structure:

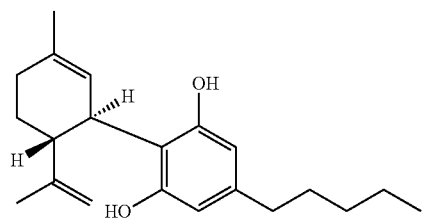

CBD is a cannabinoid, which may be produced synthetically, or extracted from *Cannabis* plants. In some embodiments, cannabidiol is extracted from *Cannabis* plants. Non-limiting examples of *Cannabis* plants include *Cannabis sativa*, *Cannabis indica*, or *Cannabis ruderalis*. In some embodiments, CBD is extracted from hybrid varieties of *Cannabis*. CBD may be extracted from *Cannabis* plants according to known methods in the art. Such extracts may be referred to interchangeably as a CBD extract, botanical extract, or botanical drug substance. Non-limiting extraction methods include sonication, heating under reflux, soxhlet extraction, solid-phase micro-extraction, supercritical-fluid extraction, pressurized-liquid extraction, microwave-assisted extraction, solid-phase extraction, and surfactant-mediated techniques. In some embodiments, the steps for extraction include, but are not limited, to pre-washing, drying of plant parts or freeze drying, and grinding to obtain homogenous extracted plant samples.

In some embodiments, cannabidiol is extracted using an alcohol-based extraction. In some embodiments, cannabidiol is extracted with ethanol. In some embodiments, cannabidiol is obtained using a supercritical carbon dioxide based extraction. Methods for extraction of CBD from *Cannabis* plants are described in the following patent documents which are incorporated by reference in their entirety herein: U.S. Publication No. 2019/0231833 A1, (published Aug. 1, 2019), International Publication No. 2019/020738 (published Jan. 31, 2019), International Publication No. 2004/016277 A1 (published Feb. 26, 2004), U.S. Publication No. 2019/0160393 A1 (published May 30, 2019), and International Publication No. 2004/026802 (published Jan. 4, 2004).

In some embodiments, cannabidiol is produced synthetically. As described herein, synthetic cannabidiol includes CBD analogs, CBD salts, modified CBD, and propyl cannabinoids (CBDv). Synthetic CBD has the same or similar therapeutic effects as naturally occurring CBD when administered to the subjects. Patent documents, such as U.S. Publication No. 2019/0031601 (published Jan. 31, 2019), U.S. Pat. No. 9,447,019 (issued Sep. 20, 2016), and U.S. Publication No. 2015/0320698 (published Nov. 12, 2015), which describe synthetic cannabinoids are incorporated by reference herein in their entirety.

Methods for cannabidiol synthesis are described in the following patent documents, which are incorporated by reference in their entirety herein: EP Publication No. 2578561 A1 (published Apr. 10, 2013), U.S. Publication No. 2017/0008868 A1 (published Aug. 28, 2018). In some embodiments, cannabidiol is produced in microorganisms. Methods for producing cannabidiol in microorganisms are described in U.S. Publication No. 2016/0010126 A1 (published Jan. 14, 2016) and International Publication No. 2017/139496 (published Aug. 17, 2016), which are incorporated by reference in their entireties, herein.

In some embodiments, CBD is present in a botanical extract. In such extracts, the CBD has a purity from about 95 w/w to about 100% w/w CBD. In some embodiments, the CBD has a purity of at least about 95% w/w, about 96% w/w, about 97% w/w, about 98% w/w, or about 99% w/w, including all values and ranges in between. In some embodiments, the CBD has a purity of at least about 98% w/w. In some embodiments, the CBD has a purity of at least 99% w/w. Accordingly, "CBD" as used herein refers to CBD having a purity ranging from about 95% to about 100%, e.g., at least about 98% w/w pure.

In some embodiments, the CBD extracts of the disclosure contain up to about 5% w/w of other cannabinoids and/or terpenes. In some embodiments, the CBD extracts of the disclosure contain up to about 2% w/w of other cannabinoids and/or terpenes. In some embodiments, the CBD extracts of the disclosure contain up to about 5% w/w, about 2% w/w, or up to about 1% of other cannabinoid, but is substantially free of terpenes. Indeed, the presence of these additional components may influence the pharmacological properties of the CBD administered according to the methods of the disclosure. Non-limiting examples of cannabinoids include cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), tetrahydrocannabinol (THC), cannabidiolic acid (CBDA), cannabidiol-C4 (CBD-C4), cannabidiol-C1 (CBD-C1), cannabielsoin-type-C1 (CBEI), cannabielsoin-type-C2 (CBEII), 6-OH-cannabidiol, 7-OH-cannabidiol, and tetrahydrocannabinolic acid (THCA). Non-limiting examples of terpenes include alpha-cedrene, alpha-humulene, alpha-pinene, alpha-terpinene, beta-myrcene, beta-pinene, borneol, camphene, camphor, caryophyllene oxide, cedrol, alpha-bisabolol, alpha-phellandrene, isopulegol, cis-nerolidol, 3-carene, fenchyl alcohol, hexahydrothymol, eucalyptol, isoborneol, farnesene, fenchone, gamma-terpinene, geraniol, geranyl acetate, humulene, guaiol, limonene, linalool, nerol, ocimene, alpha-phellandrene, pulegone, sabinene, sabinene hydrate, terpineol, terpinolene, trans-caryophyllene, β-caryophyllene, trans-nerolidol, and valencene.

In some embodiments, the CBD extracts of the disclosure contain up to about 1% w/w CBDV. In some embodiments, the CBD extracts of the disclosure contain about 0% w/w, about 0.05% w/w, about 0.1% w/w, about 0.15% w/w, about 0.2% w/w, about 0.25% w/w, about 0.30% w/w, about 0.35% w/w, about 0.40% w/w, about 0.45% w/w, about 0.50% w/w, about 0.55% w/w, about 0.60% w/w, about 0.65% w/w, about 0.70% w/w, about 0.75% w/w, about 0.80% w/w, about 0.85% w/w, about 0.90% w/w, about 0.95% w/w, or about 1.0% w/w CBDV, including all values and ranges in between.

In some embodiments, the CBD extracts of the disclosure contain up to about 1 w/w THC. In some embodiments, the CBD extracts of the disclosure contain about 0 w/w, about 0.05 w/w, about 0.1% w/w, about 0.15 w/w, about 0.2% w/w, about 0.25 w/w, about 0.30% w/w, about 0.35 w/w, about 0.40% w/w, about 0.45 w/w, about 0.50 w/w, about 0.55% w/w, about 0.60% w/w, about 0.65 w/w, about 0.70% w/w, about 0.75 w/w, about 0.80% w/w, about 0.85 w/w, about 0.90% w/w, about 0.95 w/w, or about 1.0% w/w THC, including all values and ranges in between.

In some embodiments, the CBD extracts of the disclosure contain up to about 0.5% w/w CBD-C4. In some embodiments, the CBD extracts of the disclosure contain about 0 w/w, about 0.05 w/w, about 0.1% w/w, about 0.15 w/w, about 0.2% w/w, about 0.25 w/w, about 0.30% w/w, about 0.35 w/w, about 0.40% w/w, about 0.45 w/w, or about 0.50 w/w CBD-C4.

In some embodiments, the CBD extracts of the disclosure contain up to about 0.15% w/w CBD-C1. In some embodiments, the CBD extracts of the disclosure contain about 0 w/w, about 0.005 w/w, about 0.01% w/w, about 0.015 w/w, about 0.02% w/w, about 0.025 w/w, about 0.030% w/w, about 0.035 w/w, about 0.040% w/w, about 0.045 w/w, about 0.050% w/w, about 0.055 w/w, about 0.060% w/w, about 0.065% w/w, about 0.070% w/w, about 0.075 w/w, about 0.080% w/w, about 0.085 w/w, about 0.090% w/w, about 0.095% w/w, about 0.10% w/w, or about 0.15% w/w CBD-C1, including all values and ranges in between.

In some embodiments, the CBD extracts of the disclosure contain up to about 0.2% w/w CBEI. In some embodiments, the CBD extracts of the disclosure contain about 0 w/w, about 0.005 w/w, about 0.01% w/w, about 0.015 w/w, about 0.02% w/w, about 0.025% w/w, about 0.030% w/w, about 0.035 w/w, about 0.040% w/w, about 0.045 w/w, about 0.050% w/w, about 0.055 w/w, about 0.060% w/w, about 0.065% w/w, about 0.070% w/w, about 0.075 w/w, about 0.080% w/w, about 0.085 w/w, about 0.090% w/w, about 0.095% w/w, about 0.10% w/w, about 0.15 w/w, or about 0.20% w/w CBEI, including all values and ranges in between.

In some embodiments, the CBD extracts of the disclosure contain up to about 0.2% w/w CBEII. In some embodiments, the CBD extracts of the disclosure contain about 0 w/w, about 0.005 w/w, about 0.01% w/w, about 0.015 w/w, about 0.02% w/w, about 0.025% w/w, about 0.030% w/w, about 0.035 w/w, about 0.040% w/w, about 0.045 w/w, about 0.050% w/w, about 0.055% w/w, about 0.060% w/w, about 0.065% w/w, about 0.070% w/w, about 0.075 w/w, about 0.080% w/w, about 0.085 w/w, about 0.090% w/w, about 0.095% w/w, about 0.10% w/w, about 0.15 w/w, or about 0.20% w/w CBEII, including all values and ranges in between.

In some embodiments, the CBD extracts of the disclosure contain up to about 0.2% w/w of a combination of CBEI and CBEII. In some embodiments, the CBD extracts of the disclosure contain about 0 w/w, about 0.005 w/w, about 0.01% w/w, about 0.015 w/w, about 0.02% w/w, about 0.025 w/w, about 0.030% w/w, about 0.035 w/w, about 0.040% w/w, about 0.045 w/w, about 0.050 w/w, about 0.055 w/w, about 0.060% w/w, about 0.065% w/w, about 0.070% w/w, about 0.075% w/w, about 0.080% w/w, about 0.085% w/w, about 0.090% w/w, about 0.095 w/w, about 0.10% w/w, about 0.15 w/w, or about 0.20% w/w of a combination of CBEI and CBEII including all values and ranges in between.

In some embodiments, the CBD extracts of the disclosure contain less than about 0.1% w/w OH-CBD. In some embodiments, the CBD extracts of the disclosure contain about 0% w/w, about 0.005 w/w, about 0.01% w/w, about 0.015% w/w, about 0.02% w/w, about 0.025% w/w, about 0.030% w/w, about 0.035 w/w, about 0.040% w/w, about 0.045 w/w, about 0.050% w/w, about 0.055% w/w, about 0.060% w/w, about 0.065% w/w, about 0.070% w/w, about 0.075 w/w, about 0.080% w/w, about 0.085 w/w, about 0.090% w/w, about 0.095% w/w, or about 0.10% w/w OH-CBD, including all values and ranges in between.

In some embodiments, the CBD extracts of the disclosure comprise CBD, at purity of at least 95% w/w (e.g., 98% w/w, or 99% w/w), and CBDA, CBDV, THC and CBD-C4. In some embodiments, the CBDA is present in an amount of about 0.15% w/w or less, e.g., about 0.15% w/w, about 0.1% w/w, about 0.05% w/w, or about 0.01% w/w, inclusive of all values and ranges between these values. In some embodiments, CBDV is present in an amount of about 1.0% w/w or less, e.g., about 1.0% w/w or less, about 0.9% w/w, about 0.8% w/w, about 0.7% w/w, about 0.6% w/w, about 0.5% w/w, about 0.4% w/w, about 0.3% w/w, about 0.2% w/w, about 0.1% w/w, about 0.09% w/w, about 0.08% w/w, about 0.07% w/w, about 0.06% w/w, about 0.05% w/w, about 0.04% w/w, about 0.03% w/w, about 0.02% w/w, about 0.01% w/w, inclusive of all values and ranges between these values. In some embodiments, THC is present in an amount of about 0.15% w/w or less, e.g., about 0.15% w/w, about 0.1% w/w, about 0.05% w/w, or about 0.01% w/w, inclusive of all values and ranges between these values. In some embodiments, CBD-C4 is present in an amount of about 0.5% w/w or less, e.g., about 0.5% w/w, about 0.4% w/w, about 0.3% w/w, about 0.2% w/w, about 0.1% w/w, about 0.09% w/w, about 0.08% w/w, about 0.07% w/w, about 0.06% w/w, about 0.05% w/w, about 0.04% w/w, about 0.03% w/w, about 0.02% w/w, about 0.01% w/w, inclusive of all values and ranges between these values.

In some embodiments, CBD is administered at a dose from about 1 mg/kg/day to about 25 mg/kg/day. In some embodiments, CBD is administered at a dose from about 5 mg/kg/day to about 50 mg/kg/day. In some embodiments, CBD is administered at a dose of about 1 mg/kg/day, about 2 mg/kg/day, about 3 mg/kg/day, about 4 mg/kg/day, about 5 mg/kg/day, about 6 mg/kg/day, about 7 mg/kg/day, about 8 mg/kg/day, about 9 mg/kg/day, about 10 mg/kg/day, or about 11 mg/kg/day, about 12 mg/kg/day, about 13 mg/kg/day, about 14 mg/kg/day, or about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, about 24 mg/kg/day, about 25 mg/kg/day, about 26 mg/kg/day, about 27 mg/kg/day, about 28 mg/kg/day, about 29 mg/kg/day, about 30 mg/kg/day, about 31 mg/kg/day, about 32 mg/kg/day, about 33 mg/kg/day, about 34 mg/kg/day, about 35 mg/kg/day, about 36 mg/kg/day, about 37 mg/kg/day, about 38 mg/kg/day, about 39 mg/kg/day, about 40 mg/kg/day, about 41 mg/kg/day, about 42 mg/kg/day, about 43 mg/kg/day, about 44 mg/kg/day, about 45 mg/kg/day, about 46 mg/kg/day, about 47 mg/kg/day, about 48 mg/kg/day, about 49 mg/kg/day, or about 50 mg/kg/day. In some embodiments, CBD is administered at a dose of about 5 mg/kg/day. In some embodiments, CBD is administered at a dose of about 10 mg/kg/day. In some embodiments, CBD is administered at a dose of about 15 mg/kg/day. In some embodiments, CBD is administered at a dose of about 20 mg/kg/day. In some embodiments, CBD is administered at a dose of about 25 mg/kg/day. In some embodiments, CBD is administered at a dose of about 50 mg/kg/day.

In some embodiments, CBD is administered at a dose of about 2.5 mg/kg to about 12.5 mg/kg twice daily. In some embodiments, CBD is administered at a dose from about 2.5 mg/kg to about 25 mg/kg twice daily. In some embodiments, CBD is administered at a dose of about 2.5 mg/kg, 3 mg/kg/, 3.5 mg/kg, 4.0 mg/kg, 4.5 mg/kg, 5 mg/kg, about 6 mg/kg, about 7 mg/kg, about 8 mg/kg, about 9 mg/kg, about 10 mg/kg, or about 11 mg/kg/day, about 12 mg/kg, about 12.5 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, or about 25 mg/kg. In some embodiments, CBD is administered at a dose of about 2.5 mg/kg twice daily. In some embodiments, CBD is administered at a dose of about 5 mg/kg twice daily. In some embodiments, CBD is administered at a dose of about 10 mg/kg twice daily. In some embodiments, CBD is administered at a dose of about 12.5 mg/kg twice daily.

As disclosed herein, in some embodiments, CBD is administered at a reduced dose when CBD is coadministered with everolimus. A "reduced dose" of CBD is less than the dose that an otherwise identical patient with TSC would receive if said patient were not coadministered everolimus. In other words, the reduced dose of CBD administered to a patient with TSC as a combination therapy is less than the dose of CBD administered to the same (or similar) TSC patient that is not coadministered everolimus.

In some embodiments, Applicant contemplates the dose of CBD administered to a TSC patient based on the approved dosing range of EPIDIOLEX® for treating seizures in patents with Lennox-Gastaut or Dravet Syndrome. In some embodiments, Applicant contemplates that the approved dosing range of CBD in the absence of everolimus for TSC will be 5 mg/kg/day to 25 mg/kg/day. In some embodiments, Applicant contemplates that patients will be treated with about 10 mg/kg/day, about 15 mg/kg/day, about 20 mg/kg/day, or about 25 mg/kg/day in the absence of everolimus. In particular embodiments, Applicant contemplates that patients will be treated with about 10 mg/kg/day, about 15 mg/kg/day, or about 20 mg/kg/day, in the absence of everolimus.

Therapeutically effective doses will vary depending on the severity of the symptoms. As discussed herein, the methods of the present disclosure provide administering a reduce dose of CBD relative to the dose that would be therapeutically effective in the absence of everolimus. In some embodiments, the therapeutically effective dose of CBD for TSC will be 10 mg/kg/day. Accordingly, in embodiments, the reduced dose of CBD for such a patient is less than 10 mg/kg/day, e.g. 1 mg/kg/day, 2 mg/kg/day, 3 mg/kg/day, 4 mg/kg/day, 5 mg/kg/day, 6 mg/kg/day, 7 mg/kg/day, 8 mg/kg/day, or 9 mg/kg/day.

In some embodiments, the therapeutically effective dose of CBD for TSC will be 15 mg/kg/day. Accordingly, in some embodiments, the reduced dose of CBD for such a patient is less than 15 mg/kg/day, e.g. 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9 mg/kg/day, 10 mg/kg/day, 11 mg/kg/day, 12 mg/kg/day, 13 mg/kg/day, or 14 mg/kg/day.

In some embodiments, the therapeutically effective dose of CBD for TSC will be 20 mg/kg/day. Accordingly, in some embodiments, the reduced dose of TSC for such a patient is less than 20 mg/kg/day, e.g. 1 mg/kg/day, 2 mg/kg/day, 3 mg/kg/day, 4 mg/kg/day, 5 mg/kg/day, 6 mg/kg/day, 7 mg/kg/day, 8 mg/kg/day, or 9 mg/kg/day, 10 mg/kg/day, 11 mg/kg/day, 12 mg/kg/day, 13 mg/kg/day, 14 mg/kg/day, 15 mg/kg/day, 16 mg/kg/day, 17 mg/kg/day, 18 mg/kg/day, or 19 mg/kg/day.

In some embodiments, the therapeutically effective dose of CBD for TSC will be 25 mg/kg/day. Accordingly, in some embodiments, the reduced dose of CBD for such a patient is less than 25 mg/kg/day, e.g. 1 mg/kg/day, 2 mg/kg/day, 3 mg/kg/day, 4 mg/kg/day, 5 mg/kg/day, 6 mg/kg/day, 7 mg/kg/day, 8 mg/kg/day, or 9 mg/kg/day, 10 mg/kg/day, 11 mg/kg/day, 12 mg/kg/day, 13 mg/kg/day, 14 mg/kg/day, 15 mg/kg/day, 16 mg/kg/day, 17 mg/kg/day, 18 mg/kg/day, 19 mg/kg/day, 20 mg/kg/day, 21 mg/kg/day, 22 mg/kg/day, 23 mg/kg/day, or 24 mg/kg/day.

In some embodiments, the reduced dose of CBD administered to a TSC patient in combination with everolimus is from about 10% to about 75% less than the dose of CBD administered to the same TSC patient in the absence of everolimus. In some embodiments, the reduced dose of CBD administered to a TSC patient in combination with everolimus is about 10%, about 15%, about 20%, about 25%, about 30%, about 35%, about 40%, about 45%, about 50%, about 55%, about 60%, about 65%, about 70%, or about 75% less than the dose of CBD administered to the same TSC patient in the absence of everolimus, including all values and ranges between these values.

In some embodiments, the reduced dose of CBD administered to a TSC patient in combination with everolimus is reduced by at least about 1 mg/kg/day, about 2 mg/kg/day, about 3 mg/kg/day, about 4 mg/kg/day, about 5 mg/kg/day, about 6 mg/kg/day, about 7 mg/kg/day, about 8 mg/kg/day, about 9 mg/kg/day, about 10 mg/kg/day, about 11 mg/kg/day, about 12 mg/kg/day, about 13 mg/kg/day, about 14 mg/kg/day, about 15 mg/kg/day, about 16 mg/kg/day, about 17 mg/kg/day, about 18 mg/kg/day, about 19 mg/kg/day, or about 20 mg/kg/day compared to the dose of CBD the patient would receive in the absence of everolimus, including all values and ranges between these values. In some embodiments, the reduced dose of CBD administered to a TSC patient in combination with everolimus is reduced by at least about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, or about 20 mg/kg compared to the dose of CBD the patient would receive in the absence of everolimus, including all values and ranges between these values.

In some embodiments, the reduced dose of CBD ranges from about 1 mg/kg/day to about 23 mg/kg/day. In some embodiments, the reduced dose of CBD is about 1 mg/kg/day, about 2 mg/kg/day, about 2.5 mg/kg/day, about 3 mg/kg/day, about 4 mg/kg/day, about 5 mg/kg/day, about 6 mg/kg/day, about 7 mg/kg/day, about 8 mg/kg/day, about 9 mg/kg/day, about 10 mg/kg/day, or about 11 mg/kg/day, about 12 mg/kg/day, about 12.5 mg/kg/day, about 13 mg/kg/day, about 14 mg/kg/day, or about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, or about 23 mg/kg/day, including all values and ranges in between. In some embodiments, the reduced dose of CBD is about 5 mg/kg/day. In some embodiments, the reduced dose of CBD is about 10 mg/kg/day. In some embodiments, the reduced dose of CBD is about 15 mg/kg/day. In some embodiments, the reduced dose of CBD is about 20 mg/kg/day.

In some embodiments, coadminstration of CBD (at 25 mg/kg/day) with everolimus elevates the pharmacokinetics parameters (Cmax and AUC) of everolimus by 2.5 fold. In some embodiments, the dose of CBD is reduced such that the pharmacokinetics parameters (Cmax and AUC) of everolimus are increased by no more than 2.4 2.3, 2.2, 2.1, 2.0, 1.9, 1.8, 1.7, 1.6, 1.5, 1.4, 1.3, 1.2, 1.1, or 1.0.

According to the current FDA label, CBD is administered at an starting dose of 5 mg/kg/day in patients with normal hepatic status or mild hepatic impairment. CBD causes dose-related elevations of liver transaminases (alanine aminotransferase (ALT) and/or aspartate aminotransferase (AST)). A lower starting dose compared to maintenance dose (e.g. the lowest dose of drug that achieves efficacy and minimizes side effects) is important to adapt the liver to CBD, such that it can increase CBD metabolism and reduce the incidences of dose-related elevations of liver transaminases ALT and/or AST.

If the starting dose is tolerated and additional seizure reduction is required, the maintenance dose of CBD can be increased to a maximum dose of 25 mg/kg/day (in the absence of everolimus). Because CBD can cause elevation of liver transaminases, the serum concentration of these enzymes is monitored.

Due to the DDI with everolimus, in some embodiments, the starting dose of CBD is reduced from the currently approved starting dose of 5 mg/kg/day. In some embodiments, CBD (when coadministered with everolimus) will be administered at a starting dose from about 1 mg/kg/day to about 4 mg/kg/day (e.g., about 1 mg/kg/day, about 1.5 mg/kg/day, about 2 mg/kg/day, about 2.5 mg/kg/day, about 3 mg/kg/day, about 3.5 mg/kg/day, or about 4 mg/kg/day), and the dose of CBD will be increased up to maximum dose of e.g., about 10 mg/kg/day, about 15 mg/kg/day, about 20 mg/kg/day, or 24 mg/kg/day.

In some embodiments, the starting dose of CBD may be increased for efficacy. In some embodiments, the dose of CBD may be increased in increments of about 0.5 mg/kg/day to about 5 mg/kg/day. In some embodiments the dose of CBD may be increased by about 0.5 mg/kg/day, about 1.0 mg/kg/day, about 1.5 mg/kg/day, about 2.0 mg/kg/day, about 2.5 mg/kg/day, about 3.0 mg/kg/day, about 3.5 mg/kg/day, about 4.0 mg/kg/day, about 4.5 mg/kg/day, or about 5.0 mg/kg/day.

In some embodiments, the dose of CBD may be increased every day, every other day, every third day, every fourth day, every fifth day, every sixth day, or every seventh day, every two weeks, every three weeks, every four weeks, every five weeks, every month, every two months, or every year. In some embodiments, the dose of CBD may be increased from the starting dose after one week. Dose increases may occur once per week thereafter.

In some embodiments, after administering between about 1 mg/kg/day and about 50 mg/kg/day of CBD (e.g. about 1.0 mg/kg/day, about 2.0 mg/kg/day, about 2.5 mg/kg/day, about 3.0 mg/kg/day, about 3.5 mg/kg/day, about 4.0 mg/kg/day, about 5.0 mg/kg/day, about 6.0 mg/kg/day, about 7.5 mg/kg/day, about 8 mg/kg/day, about 9 mg/kg/day, about 10 mg/kg/day, about 11 mg/kg/day, about 12 mg/kg/day, about 13 mg/kg/day, about 14 mg/kg/day, about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, about 24 mg/kg/day, about 25 mg/kg/day, about 26 mg/kg/day, about 27 mg/kg/day, about 28 mg/kg/day, about 29 mg/kg/day, about 30 mg/kg/day, about 31 mg/kg/day, about 32 mg/kg/day, about 33 mg/kg/day, about 34 mg/kg/day, about 35 mg/kg/day, about 36 mg/kg/day, about 37 mg/kg/day, about 38 mg/kg/day, about 39 mg/kg/day, about 40 mg/kg/day, about 41 mg/kg/day, about 42 mg/kg/day, about 43 mg/kg/day, about 44 mg/kg/day, about 45 mg/kg/day, about 46 mg/kg/day, about 47 mg/kg/day, about 48 mg/kg/day, about 49 mg/kg/day, or about 50 mg/kg/day), the patient has an steady state area under the concentration time curve from time zero (t1) to five hours (t2) ($AUC_{t1-t2}$) between 25 ng*hr/mL and 4000 ng*hr/mL. In some embodiments, the $AUC_{t1-t2}$ is about 25 ng*hr/mL, about 50 ng*hr/mL, about 75 ng*hr/mL, about 100 ng*hr/mL, about 125 ng*hr/mL, about 150 ng*hr/mL, about 175 ng*hr/mL, about 200 ng*hr/mL, about 225 ng*hr/mL, about 250 ng*hr/mL, about 275 ng*hr/mL, about 300 ng*hr/mL, about 325 ng*hr/mL, about 350 ng*hr/mL, about 375 ng*hr/mL, and about 400 ng*hr/mL, about 500 ng*hr/mL, about 600 ng*hr/mL, about 700 ng*hr/mL, about 800 ng*hr/mL, about 900 ng*hr/mL, about 1000 ng*hr/mL, about 1100 ng*hr/mL, about 1200 ng*hr/mL, about 1300 ng*hr/mL, about 1400 ng*hr/mL, about 1500 ng*hr/mL, about 1600 ng*hr/mL, about 1700 ng*hr/mL, about 1800 ng*hr/mL, about 1900 ng*hr/mL, about 2000 ng*hr/mL, about 2100 ng*hr/mL, about 2200 ng*hr/mL, about 2300 ng*hr/mL, about 2400 ng*hr/mL, about 2500 ng*hr/mL, about 2600 ng*hr/mL, about 2700 ng*hr/mL, about 2800 ng*hr/mL, about 2900 ng*hr/mL, about 3000 ng*hr/mL, about 3100 ng*hr/mL, about 3200 ng*hr/mL, about 3300 ng*hr/mL, about 3400 ng*hr/mL, about 3500 ng*hr/mL, about 3600 ng*hr/mL, about 3700 ng*hr/mL, about 3800 ng*hr/mL, about 3900 ng*hr/mL, about or about 4000 ng*hr/mL, including all ranges and values in between. In some embodiments, the $AUC_{t1-t2}$ is between 80% and 125% of the aforementioned values.

In some embodiments, the $AUC_{t1-t2}$ is reported as a geometric mean (% coefficient of variation). In some embodiments, after administration of everolimus and CBD, the patient has an $AUC_{t1-t2}$ of CBD that is bioequivalent to 25 mg/kg/day of CBD—i.e., an $AUC_{t1-t2}$ ranging from 80% to about 125% of 2520 (52.4%) ng*hr/mL. In some embodiments, after administration of everolimus and CBD, the patient has an $AUC_{t1-t2}$ of CBD that is less than $AUC_{t1-t2}$ of 50 mg/kg/day of CBD—i.e., less than 2730 (87.2%) ng*hr/mL (e.g., less than 2700 ng*hr/mL, 2600 ng*hr/mL, 2500 ng*hr/mL, 2400 ng*hr/mL, 2300 ng*hr/mL, 2200 ng*hr/mL, 2100 ng*hr/mL, 2000 ng*hr/mL, 1900 ng*hr/mL, 1800 ng*hr/mL, 1700 ng*hr/mL, 1600 ng*hr/mL, 1500 ng*hr/mL, 1400 ng*hr/mL, 1300 ng*hr/mL, 1200 ng*hr/mL, 1100 ng*hr/mL, or 1000 ng*hr/mL, etc).

In some embodiments, after administration of everolimus and CBD, the patient has a steady state AUC of CBD from time zero to the last detectable dose (t) ($AUC_{0-t}$) that is bioequivalent to 5 mg/kg/day of CBD—i.e., an $AUC_{0-t}$ ranging from 80% to about 125% of 241 (101) ng*hr/mL. In some embodiments, after administration of everolimus and CBD, the patient has an $AUC_{0-t}$ of CBD that is bioequivalent to 10 mg/kg/day of CBD—i.e., an $AUC_{0-t}$ ranging from 80% to about 125% of 722 (79.9) ng*hr/mL. In some embodiments, after administration of everolimus and CBD, the patient has an $AUC_{0-t}$ of CBD that is bioequivalent to 20 mg/kg/day of CBD—i.e., an $AUC_{0-t}$ ranging from 80% to about 125% of 963 (93.4) ng*hr/mL.

Everolimus

Everolimus is an inhibitor of mammalian target of rapamycin (mTOR), a serine-threonine kinase, downstream of the PI3K/AKT pathway. Everolimus binds to the intracellular protein FKBP-12, resulting in an inhibitory complex formation with mTOR complex 1 (mTORC1) and inhibition of mTOR kinase activity. Everolimus reduces the activity of S6 ribosomal protein kinase (S6K1) and eukaryotic elongation factor 4E-binding protein (4E-BP1), downstream effectors of mTOR, which are involved in protein synthesis. S6K1 is a substrate of mTORC1 and phosphorylates the activation domain 1 of the estrogen receptor which results in ligand-independent activation of the receptor. In addition, everolimus inhibits the expression of hypoxia-inducible factor (e.g., HIF-1) and reduced the expression of vascular endothelial growth factor (VEGF). Inhibition of mTOR by everolimus has been shown to reduce cell proliferation, angiogenesis, and glucose uptake in in vitro and/or in vivo studies.

Constitutive activation of the PI3K/Akt/mTOR pathway can contribute to endocrine resistance in breast cancer. In vitro studies show that estrogen-dependent and HER2+ breast cancer cells are sensitive to the inhibitory effects of everolimus, and that combination treatment with everolimus and Akt, HER2, or aromatase inhibitors enhances the antitumor activity of everolimus in a synergistic manner.

Two regulators of mTORC1 signaling are the oncogene suppressors tuberin-sclerosis complexes 1 and 2 (TSC1, TSC2). Loss or inactivation of either TSC1 or TSC2 leads to activation of downstream signaling. In tuberous sclerosis complex, inactivating mutations in either the TSC1 or the TSC2 gene lead to hamartoma formation throughout the body.

Everolimus is approved by the FDA for treatment of the following conditions: treatment of postmenopausal women with advanced hormone receptor-positive, HER2-negative breast cancer (advanced HR+BC) in combination with exemestane after failure of treatment with letrozole or anstrozole; adults with progressive neuroendocrine tumors of pancreatic origin (PNET) that are unresectable, locally advanced or metastatic; adults with advanced renal cell carcinoma (RCC) after failure of treatment with sunitinib or sorafenib; adults with renal angiomyolipoma and TSC, not requiring immediate surgery; and, pediatric and adult patients with TSC who have subependymal giant cell astrocytoma (SEGA) that requires therapeutic intervention but cannot be curatively resected; the prophylaxis of organ rejection in adult patients, including kidney transplant in combination with basiliximab, cyclosporine (reduced doses) and corticosteroids and liver transplant in combination with tacrolimus (reduced doses) and corticosteroids.

Everolimus has the following structure:

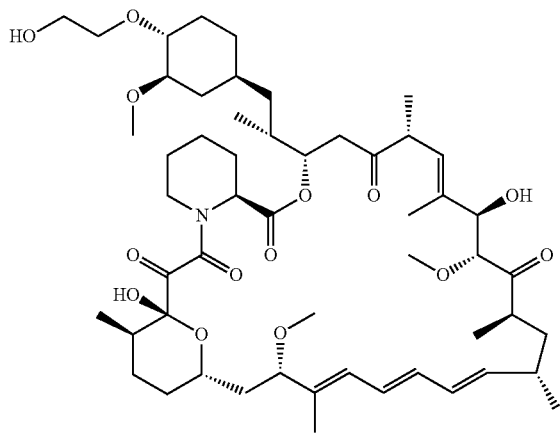 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

The recommended dosage of everolimus for TSC-associated renal angiomyolipoma is 10 mg orally once daily. The recommended dosage of everolimus for TSC-associated subependymal giant cell astrocytoma (SEGA) is 4.5 mg/m$^2$ orally once daily. The recommended dosage of everolimus for TSC-associated partial-onset seizures is 5 mg/m$^2$ orally once daily In some embodiments, everolimus is administered at a dose ranging from about 2 mg to about 10 mg. In some embodiments, about 2 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, or about 10.0 mg of everolimus is administered. In some embodiments, the dose of everolimus is 2.5 mg of everolimus. In some embodiments, the dose of everolimus is 5 mg of everolimus. In some embodiments, the dose of everolimus is 7.5 mg of everolimus. In some embodiments, the dose of everolimus is 10 mg of everolimus. In some embodiments, if the patient's body surface area (BSA) ranges from 0.5 m$^2$ to 1.2 m$^2$, the dose of everolimus is 2.5 mg once daily. In some embodiments, if the patient's BSA ranges from 1.3 m$^2$ to 2.1 m$^2$, the dose of everolimus is 5 mg once daily. In some embodiments, if the patient's BSA is greater than or equal to 2.2 m$^2$, the dose of everolimus is 7.5 mg once daily.

In some embodiments, everolimus is administered at a dose ranging from about 2.5 mg/m$^2$ to about 5.5 mg/m$^2$, e.g., about 2.5 mg/m$^2$, about 3.0 mg/m$^2$, about 3.5 mg/m$^2$, about 4.0 mg/m$^2$, about 4.5 mg/m$^2$, about 5.0 mg/m$^2$, or about 5.5 mg/m$^2$, inclusive of all values and ranges between these values. In some embodiments, the dose of everolimus is 5.0 mg/m$^2$ of everolimus. In some embodiments, the dose of everolimus is 4.5 mg/m$^2$ of everolimus. In some embodiments, the dose of everolimus is 2.5 mg/m$^2$ of everolimus.

In some embodiments, everolimus is administered in an amount sufficient to attain trough concentrations of 5 ng/mL to 15 ng/mL. When trough levels exceed 15 ng/mL are not tolerable, and present a risk of adverse events, such as gastrointestinal disorders (vomiting, diarrhea, constipation), hyperlipidemia, respiratory tract infection, nasopharyngitis, pyrexia, interstitial pneumonitis, edema, mouth ulcers, impaired wound healing, hematotoxicity, stomatitis, renal failure, and rash.

In some embodiments, everolimus is administered once daily.

In some embodiments, everolimus is administered every day, every other day, every third day, every fourth day, every fifth day, every sixth day, every week, every 2 weeks, every month, or every year. In some embodiments, everolimus is administered every day. In some embodiments, everolimus is administered every other day.

In some embodiments, a starting dose of about 4.5 mg/m$^2$ of everolimus is administered, and the dose of everolimus is adjusted to obtain trough concentrations of about 5 ng/mL to about 15 ng/mL.

In some embodiments, a starting dose of about 5.0 mg/m$^2$ of everolimus is administered, and the dose of everolimus is adjusted to obtain trough concentrations of about 5 ng/mL to about 15 ng/mL. In some embodiments, the dose is adjusted to about 5.5 mg/m$^2$, about 6 mg/m$^2$, about 6.5 mg/m$^2$, about 7 mg/m$^2$, about 7.5 mg/m$^2$, about 8 mg/m$^2$, about 8.5 mg/m$^2$, 9 mg/m$^2$, about 9.5 mg/m$^2$, or to about 10 mg/m$^2$, including all values and ranges between these values.

In some embodiments, the dose of everolimus is increased from the starting dose. In some embodiments, the dose of everolimus is decreased from the starting dose. In some embodiments, the dose of everolimus administered is reduced by 5%, 10%, 15%, 20%, 25%, 30%, 35%, 40%, 45%, or 50%, including all values and ranges therebetween.

Everolimus is metabolized by CYP3A4, CYP3A5, and CYP2C8. Following oral administration of everolimus, everolimus is the main circulating component in the blood. Six main metabolites of everolimus have been detected in human blood, including three monohydroxylated metabolites, two hydrolytic ring-opened products, and a phosphatidylcholine conjugate of everolimus.

Everolimus is a substrate of CYP3A4 and P-gp. The FDA label for everolimus suggests avoiding the concomitant use of strong P-gp and strong CYP3A4 inhibitors and reducing the dose of everolimus with a P-gp and moderate CYP3A4 inhibitor (Table 1 and Table 2).

TABLE 1

Recommended Dosage Modifications for Concurrent Use of Everolimus with a P-gp and moderate CYP3A4 inhibitor

| Indication | Dose Modification for Everolimus |
|---|---|
| Breast Cancer, NET, RCC, and TSC-Associated Renal Angiomyolipoma | Reduce dose to 2.5 mg once daily. May increase dose to 5 mg once daily if tolerated. Resume dose administered prior to inhibitor initiation, once the inhibitor is discontinued for 3 days. |
| TSC-Associated SEGA and TSC- Associated Partial-Onset Seizures | Reduce the daily dose by 50%. Change to every other day dosing if the reduced dose is lower than the lowest available strength. Resume dose administered prior to inhibitor initiation, once the inhibitor is discontinued for 3 days. |

TABLE 2

Recommended Dosage Modifications for Concurrent Use of Everolimus with a P-gp and strong CYP3A4 inducer

| Indication | Dose Modification for Everolimus |
|---|---|
| Breast Cancer, NET, RCC, and TSC- Associated Renal Angiomyolipoma | Avoid coadministration where alternatives exist. If coadministration cannot be avoided, double the daily dose using increments of 5 mg or less. Multiple increments may be required. Resume dose administered prior to inducer initiation, once the inducer is discontinued for 5 days. |
| TSC-Associated SEGA and TSC- Associated Partial-Onset Seizures | Double the daily dose using increments of 5 mg or less. Multiple increments may be required. Addition of another strong CYP3A4 inducer in a patient already receiving treatment with a strong CYP3A4 inducer may not require additional dosage Assess trough concentrations when initiating and discontinuing the inducer Resume the dose administered before starting any inducer, once all inducers are discontinued for 5 days. |

After administration of everolimus in patients with advanced solid tumors, peak everolimus concentrations are reached 1 to 2 hours after administration of oral doses ranging from 5 mg to 70 mg. Following single doses, Cmax is dose proportional with daily dosing between 5 mg and 10 mg. With single doses of 20 mg and higher, the increase in Cmax is less than dose-proportional; however, AUC shows dose-proportionality over the 5 mg to 70 mg dose range. Steady-state was achieved within 2 weeks following once-daily dosing. In patients with TSC-associated SEGA, everolimus Cmin was approximately dose-proportional within the dose range from 1.35 mg/m$^2$ to 14.4 mg/m$^2$.

Everolimus area under the curve (AUC) is linear in the dose range from 2.5 mg to 70 mg.

In some embodiments, after administering between about 1 mg and about 20 mg (e.g., 1.0 mg, 2.0 mg, 2.5 mg, 3.0 mg, 3.5 mg, 4.0 mg, 5.0 mg, 6.0 mg, 7.5 mg, 8 mg, 9 mg, 10 mg, 11 mg, 12 mg, 13 mg, 14 mg, 15 mg, 20 mg) of everolimus, the patient has a maximum observed plasma drug concentration ($C_{max}$ss) between 1 ng/mL and 200 ng/mL. In some embodiments, the $C_{max}$ss is about 1 ng/mL, about 5 ng/mL, about 10 ng/mL, about 15 ng/mL, about 20 ng/mL, about 21.6 ng/mL, about 25 ng/mL, about 30 ng/mL, about 35 ng/mL, about 40 ng/mL, about 45 ng/mL, about 50 ng/mL, about 55 mg/mL, about 60 ng/mL, about 65 mg/mL, about 70 ng/mL, about 75 ng/mL, about 80 ng/mL, about 85 ng/mL, about 90 ng/mL, about 95 ng/mL, about 100 ng/mL, about 105 ng/mL, about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL, including all ranges and values in between. In some embodiments, the $C_{max}$ss is between 80% and 125% of any of the aforementioned values or ranges between the aforementioned values.

In some embodiments, the $C_{max}$ss is reported as a geometric mean±Standard Deviation (SD). In some embodiments, after administration of everolimus and CBD, the patient has a $C_{max}$ss of everolimus that is bioequivalent to 2.5 mg of everolimus—i.e., a $C_{max}$ss ranging from 80% to about 125% of 62.1±13.1 ng/mL. In some embodiments, after administration of everolimus and CBD, the patient has a $C_{max}$ss of everolimus that is bioequivalent to 5 mg of everolimus—i.e., a $C_{max}$ss ranging from 80% to about 125% of 114±36 ng/mL. In some embodiments, after administration of everolimus and CBD, the patient has a $C_{max}$ss of everolimus that is bioequivalent to 10 mg of everolimus— i.e., a $C_{max}$ss ranging from 80% to about 125% of 139 ng/mL. In some embodiments, after administration of everolimus and CBD, the patient has a $C_{max}$ss of everolimus that within the range of the $C_{max}$ss of 2.5 mg and $C_{max}$ss the of 10 mg.

In some embodiments, after administering between about 1 mg and about 20 mg (e.g., 1.0 mg, 2.0 mg, 2.5 mg, 3.0 mg, 3.5 mg, 4.0 mg, 5.0 mg, 6.0 mg, 7.5 mg, 8 mg, 9 mg, 10 mg, 11 mg, 12 mg, 13 mg, 14 mg, 15 mg, 20 mg) of everolimus, the patient has a minimum observed steady state plasma drug concentration ($C_{min}$ss) of everolimus between 1 ng/mL and 100 ng/mL. In some embodiments, the $C_{min}$ss is about 1 ng/mL, about 5 ng/mL, about 10 ng/mL, about 15 ng/mL, about 20 ng/mL, about 21.6 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 mg/mL, about 70 ng/mL, about 75 ng/mL, about 80 ng/mL, about 85 ng/mL, about 90 ng/mL, about 95 ng/mL, or about 100 ng/mL, including all ranges and values in between. In some embodiments, the $C_{min}$ss is between 80% and 125% of any of the aforementioned values or ranges between the aforementioned values.

In some embodiments, the $C_{min}$ss is reported as a geometric mean±Standard Deviation (SD). In some embodiments, after administration of everolimus and CBD, the patient has a $C_{min}$ss of everolimus that is bioequivalent to 2.5 mg of everolimus—i.e., a $C_{min}$ss ranging from 80% to about 125% of 13.6±9.0 ng/mL. In some embodiments, after administration of everolimus and CBD, the patient has a $C_{min}$ss of everolimus that is bioequivalent to 5 mg of everolimus—i.e., a $C_{min}$ss ranging from 80% to about 125% of 17.4±4.5 ng/mL. In some embodiments, after administration of everolimus and CBD, the patient has a $C_{min}$ss of everolimus that is bioequivalent to 10 mg of everolimus— i.e., a $C_{min}$ss ranging from 80% to about 125% of 16.5 ng/mL. In some embodiments, after administration of everolimus and CBD, the patient has a $C_{max}$ss that within the range of the $C_{min}$ss of 2.5 mg and $C_{min}$ss the of 10 mg.

In some embodiments, after administering between about 1.0 mg and about 20 mg of everolimus, the patient has a time to reach $C_{max}$ ($t_{max}$) between 0.1 hours and 2 hours. In some embodiments, the $t_{max}$ is about 0.1 hours, about 0.2 hours, about 0.3 hours, about 0.4 hours, about 0.5 hours, about 0.6 hours, about 0.7 hours, about 0.8 hours, about 0.9 hours, about 1.0 hours, about 1.1 hours, about 1.2 hours, about 1.3 hours, about 1.4 hours, about 1.5 hours, about 1.6 hours, about 1.7 hours, about 1.8 hours, about 1.9 hours, or about 2.0 hours. In some embodiments, the $t_{max}$ is between about 80% and about 125% of any of the aforementioned values or ranges between the aforementioned values.

In some embodiments, the $t_{max}$ is reported as a median (range). In some embodiments, the patient has a $t_{max}$ ranging from 80% to about 125% of 1.0 hour (1.0 hour-1.5 hours) after administration of 2.5 mg of everolimus. In some embodiments, the patient has a $t_{max}$ ranging from 80% to about 125% of 0.8 hour (0.8 hours-1.5 hours) after administration of 5 mg of everolimus. In some embodiments, the patient has a $t_{max}$ ranging from 80% to about 125% of 1.0 hours after administration of 10 mg of everolimus.

In some embodiments, after administering between about 1.0 mg and about 20 mg of everolimus (e.g. 1.0 mg, 2.0 mg, 2.5 mg, 3.0 mg, 3.5 mg, 4.0 mg, 5.0 mg, 6.0 mg, 7.5 mg, 8 mg, 9 mg, 10 mg, 11 mg, 12 mg, 13 mg, 14 mg, 15 mg, 20 mg), the patient has an area under the concentration time curve from zero hours to twenty four hours ($AUC_{24}$) between 100 ng*hr/mL and 2000 ng*hr/mL. In some embodiments, the $AUC_{24}$ is about 25 ng*hr/mL, about 50 ng*hr/mL, about 75 ng*hr/mL, about 100 ng*hr/mL, about 125 ng*hr/mL, about 150 ng*hr/mL, about 175 ng*hr/mL, about 200 ng*hr/mL, about 225 ng*hr/mL, about 250 ng*hr/mL, about 275 ng*hr/mL, about 300 ng*hr/mL, about 325 ng*hr/mL, about 350 ng*hr/mL, about 375 ng*hr/mL, and about 400 ng*hr/mL, about 500 ng*hr/mL, about 600 ng*hr/mL, about 700 ng*hr/mL, about 800 ng*hr/mL, about 900 ng*hr/mL, about 1000 ng*hr/mL, about 1100 ng*hr/mL, about 1200 ng*hr/mL, about 1300 ng*hr/mL, about 1400 ng*hr/mL, about 1500 ng*hr/mL, about 1600 ng*hr/mL, about 1700 ng*hr/mL, about 1800 ng*hr/mL, about 1900 ng*hr/mL, or about 2000 ng*hr/mL including all ranges and values in between. In some embodiments, the $AUC_{24}$ is between 80% and 125% of the aforementioned values.

In some embodiments, the $AUC_{24}$ is reported as a geometric mean±Standard Deviation (SD). In some embodiments, after administration of everolimus and CBD, the patient has an $AUC_{24}$ that is bioequivalent to 2.5 mg of everolimus—i.e., an $AUC_{24}$ ranging from 80% to about 125% of 570±195 ng*hr/mL. In some embodiments, after administration of everolimus and CBD, the patient has an $AUC_{24}$ that is bioequivalent to 5 mg of everolimus—i.e., an $AUC_{24}$ ranging from 80% to about 125% of 716±123 ng*hr/mL. In some embodiments, after administration of everolimus and CBD, the patient has an $AUC_{24}$ that is bioequivalent to 10 mg of everolimus—i.e., an $AUC_{24}$ ranging from 80% to about 125% of 1470 ng*hr/mL.

In some embodiments, the methods of disclosure provide for dose reductions to achieve everolimus blood plasma trough concentrations ranging from 5-15 ng/mL, e.g., about 5, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL or 15 ng/mL, inclusive of all values and ranges between these values.

In some embodiments, the methods of the disclosure provide for dose reductions to achieve maximum blood plasma concentrations of everolimus less than 46 mg/mL, e.g., about 45 ng/mL, about 44 ng/mL, about 43 ng/mL, about 42 ng/mL, about 41 ng/mL, about 40 ng/mL, about 39 ng/mL, about 38 ng/mL, about 37 ng/mL, about 36 ng/mL, 35 ng/mL, about 34 ng/mL, about 33 ng/mL, about 32 ng/mL, about 31 ng/mL, about 30 ng/mL, about 29 ng/mL, about 28 ng/mL, about 27 ng/mL, about 26 ng/mL, 25 ng/mL, about 24 ng/mL, about 23 ng/mL, about 22 ng/mL, about 21 ng/mL, about 20 ng/mL, about 19 ng/mL, about 18 ng/mL, about 17 ng/mL, about 16 ng/mL, 15 ng/mL, inclusive of all values and ranges between these values.

In some embodiments, the methods of the disclosure provide for dose reductions to achieve an $AUC_{0-last}$ of less than 500 n*ng/mL, e.g., about 490 n*ng/mL, about 480 n*ng/mL, about 460 n*ng/mL, about 450 n*ng/mL, about 440 n*ng/mL, about 430 n*ng/mL, about 420 n*ng/mL, about 410 n*ng/mL, about 400 n*ng/mL, about 390 n*ng/mL, about 380 n*ng/mL, about 360 n*ng/mL, about 350 n*ng/mL, about 340 n*ng/mL, about 330 n*ng/mL, about 320 n*ng/mL, about 310 n*ng/mL, about 200 n*ng/mL, about 190 n*ng/mL, about 180 n*ng/mL, about 160 n*ng/mL, about 150 n*ng/mL, about 140 n*ng/mL, about 130 n*ng/mL, about 120 n*ng/mL, about 110 n*ng/mL, or about 100 n*ng/mL, inclusive of all values and ranges therebetween.

In some embodiments, the methods of the disclosure provide for dose reductions to achieve an $AUC_{0-inf}$ of less than 530 n*ng/mL, e.g., about 520 n*ng/mL, about 510 n*ng/mL, about 500 n*ng/mL, about 490 n*ng/mL, about 480 n*ng/mL, about 460 n*ng/mL, about 450 n*ng/mL, about 440 n*ng/mL, about 430 n*ng/mL, about 420 n*ng/mL, about 410 n*ng/mL, about 400 n*ng/mL, about 390 n*ng/mL, about 380 n*ng/mL, about 360 n*ng/mL, about 350 n*ng/mL, about 340 n*ng/mL, about 330 n*ng/mL, about 320 n*ng/mL, about 310 n*ng/mL, about 200 n*ng/mL, about 190 n*ng/mL, about 180 n*ng/mL, about 160 n*ng/mL, about 150 n*ng/mL, about 140 n*ng/mL, about 130 n*ng/mL, about 120 n*ng/mL, about 110 n*ng/mL, or about 100 n*ng/mL, inclusive of all values and ranges therebetween.

Methods of Evaluating CBD/Everolimus Efficacy

The therapeutically effective dose of CBD may be determined in clinical trials. For example, in some embodiments, dose-escalation may be to determine the therapeutically effective dose of CBD. Dose-escalation studies are describe, for example, in NCT02544750. The efficacy of a particular dose may be evaluated by determining the incidence of adverse events and the efficacy of the particular dose. Non-limiting examples of measures to determine efficacy include change in seizure frequency, number of treatment responders, number of patients with worsening, no change, or improvements in seizure frequency, change in composite focal seizure score, change in number of seizure-free days, change in the number of seizures by subtype, change in overall condition as assessed by the participant/caregiver, change in overall condition as assessed by the physician, change in the Vineland-II score, change in Wechscler score by subtest, change in Aberrant Behavior Checklist score, change in social communication questionnaire score, change in quality of life score, change in serum IGF-1 levels, the number of participants with changes in Tanner stage, an incidence of suicidality. Clinical outcomes are generally evaluated based on changes from baseline. As used herein, "baseline" refers to a 4 week period prior to starting treatment with CBD during which clinical outcomes are measured.

In some embodiments, efficacy of treatment according to the methods of the disclosure is determined by measuring changes in seizure frequency from baseline. In some embodiments, a patient that is treated according to the methods of the disclosure exhibits a decrease in seizure frequency of at least 5%. In some embodiments, a patient that is treated according to the methods of the disclosure exhibits a decrease in seizure frequency of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more, including all values and ranges in between. In some embodiments, a patient that is treated according to the methods of the disclosure exhibits at least about a 50% decrease in seizure frequency.

In some embodiments, after treatment according to the methods of the disclosure, a patient exhibits a decrease in the number of seizures from baseline selected from the group consisting of absence, myoclonic, focal sensory, infantile, and epileptic spasms. In some embodiments, a patient that is treated according to the methods of the disclosure exhibits a decrease in myoclonic seizure frequency of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more, including all values and ranges in between. In some embodiments, a patient that is treated according to the methods of the disclosure exhibits a decrease in focal sensory seizure frequency of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more, including all values and ranges in between. In some embodiments, a patient that is treated according to the methods of the disclosure exhibits a decrease in absence seizure frequency of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more, including all values and ranges in between. In some embodiments, a patient that is treated according to the methods of the disclosure exhibits a decrease in infantile spasm frequency of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more, including all values and ranges in between. In some embodiments, a patient that is treated according to the methods of the disclosure exhibits a decrease in epileptic spasm frequency of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more, including all values and ranges in between.

In some embodiments, efficacy of treatment according to the methods of the disclosure is determined by measuring the number of treatment responders. In some embodiments, at least about 20% of patients exhibit improved symptoms of TSC after treatment according to the methods of the disclosure. In some embodiments, about 20%, about 25%, about 30%, about 35%, about 40%, about 45%, about 50%, about 55%, about 60%, about 65%, about 70%, about 75%, about 80%, about 85%, about 90%, about 95%, or more, including all values and ranges in between, exhibit improved symptoms of TSC after treatment according to the methods of the disclosure. In some embodiments, the percent change is of seizures is used to categorize the efficacy of treatments. Patients are categorized into the following groups:

(a) >25% increase in TSC seizure frequency=worsening
(b) −25%-25% change in TSC seizure frequency=no change in TSC
(c) 25%-50% decrease in TSC seizure frequency=improvement in TSC
(d) 50%-75% decrease in TSC seizure frequency=improvement in TSC
(e) >75% decrease in TSC seizure frequency=improvement in TSC In some embodiments, efficacy of treatment according to the methods of the disclosure is determined by measuring the number of patients with worsening, no change, or improvements in seizure frequency. In some embodiments, efficacy of treatment according to the methods of the disclosure is determined by measuring the number of patients with improvements in seizure frequency compared to before said treating. In some embodiments, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or about 5% of patients exhibit improvements seizure frequency after treatment according to the methods of the disclosure compared to before said treating.

In some embodiments, patients treated according to the methods of the disclosure exhibit a reduction in seizure frequency compared to before said treating. In some embodiments, patients exhibit an about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% reduction in seizure frequency compared to before said treating. In some embodiments, patients exhibit a ≥50% reduction in TSC-associated seizure frequency.

In some embodiments, patients treated according to the methods of the disclosure exhibit a reduction in the number of episodes of convulsive and non-convulsive status epilepticus. In some embodiments, after treating according to the methods of the disclosure, the number of episodes of convulsive and non-convulsive status epilepticus decreased by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, including all values and ranges in between, compared to baseline. In some embodiments, patients treated according to the methods of the disclosure exhibit a reduction in the number of episodes of convulsive status epilepticus. In some embodiments, after treating according to the methods of the disclosure, the number of episodes of convulsive status epilepticus decrease by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, including all values and ranges in between. In some embodiments, patients treated according to the methods of the disclosure exhibit a reduction in the number of episodes of non-convulsive status epilepticus. In some embodiments, after treating according to the methods of the disclosure, the number of episodes of non-convulsive status epilepticus decrease by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, including all values and ranges in between, compared to baseline.

In some embodiments, efficacy of the treatment according to the methods of the disclosure is determined by evaluating a patient's use of rescue medications. Non-limiting examples of rescue medications include benzodiazepines including diazepam, lorazepam, and midazolam. In some embodiments, after treating according to the methods of the disclosure, a patient's use of rescue medications decreases by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, including all values and ranges in between.

In some embodiments, efficacy of treatment according to the methods of the disclosure is determined by measuring the change in composite focal seizure score. In some embodiments, the composite focal seizure is calculated as the sum of: (1×Number of focal motor seizures without impairment of consciousness or awareness)+(2×Number of focal seizures with impairment of consciousness or awareness)+(3×number of focal seizures evolving to bilateral convulsive seizures). In some embodiments, after treating according to the methods of the disclosure, the composite focal seizure score decreases compared to prior to said treatment. In some embodiments, the composite focal seizure score decreases by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, or about 100%, including all values and ranges in between.

In some embodiments, efficacy of treatment according to the methods of the disclosure is determined by measuring the change in the number of seizure-free days. In some embodiments, after treating according to the methods of the disclosure, the number of seizure-free days increases by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, about 100%, about 200%, about 300%, about 400%, about 500%, or more, including all values and ranges in between.

In some embodiments, efficacy of treatment according to the methods of the disclosure is determined by measuring the change in the number of seizures by subtype. Non-limiting examples of seizure subtypes experienced by TSC patients include infantile spasm, focal, partial, tonic-clonic, atonic, myoclonic, and absence. In some embodiments, treating according to the methods of the disclosure leads to a decrease in one or more seizure subtype. In some embodiments, treating according to the methods of the disclosure leads to an about 10%, about 20%, about 30%, about 40%, about 50%, about 60%, about 70%, about 80%, about 90%, or higher reduction in the frequency of one or more seizure subtypes.

In some embodiments, efficacy of treatment according to the methods of the disclosure is determined by measuring the changes in the Vineland Adaptive Behavior Scales (VABS). The Vineland Adaptive Behavior Scales (VABS), third edition, is a standardized measure of adaptive behavior used to evaluate the personal and social skills of an individual from birth through adulthood. Individuals can be evaluated on the VABS scale by either teachers or caregivers. According to the VABS, an individual is assigned a VABS adaptive behavior composite score, which measures an individual's functioning compare to others of his or her age. An individual is also assigned domain scores in communication, daily living skills, socialization, and motor skills to assess an individual's adaptive behavior strengths and weaknesses. An individual receives a score from 20 to 140 on each of the domain scores and the VABS adaptive behavior composite score. A score from 20 to 70 represents low adaptive level. A score from 71 to 85 represents moderately low adaptive level. A score from 86 to 114 represents moderately adequate adaptive level. A score from 115 to 129 represents moderately high adaptive level. A score from 130 to 140 represents high adaptive level.

In some embodiments, after said treatment the patient experiences a reduction of symptoms associated with TSC that is characterized by at least a one point increase in the VABS adaptive behavior composite score compared to prior to the treatment. In some embodiments, the increase in the VABS adaptive behavior score is about 1 point, about 2 points, about 3 points, about 4 points, about 5 points, about 6 points, about 7 points, about 8 points, about 9 points, about 10 points, about 11 points, about 12 points, about 13 points, about 14 points, about 15 points, about 16 points, about 17 points, about 18 points, about 19 points, about 20 points, about 21 points, about 22 points, about 23 points, about 24 points, about 25 points, about 26 points, about 27 points, about 28 points, about 29 points, about 30 points, about 31 points, about 32 points, about 33 points, about 34 points, about 35 points, about 36 points, about 37 points, about 38 points, about 39 points, about 40 points, about 41 points, about 42 points, about 43 points, about 44 points, about 45 points, about 46 points, about 47 points, about 48 points, about 49 points, about 50 points, about 51 points, about 52 points, about 53 points, about 54 points, about 55 points, about 56 points, about 57 points, about 58 points, about 59 points, about 60 points, about 61 points, about 62 points, about 63 points, about 64 points, about 65 points, about 66 points, about 67 points, about 68 points, about 69 points, or about 70 points compared to prior to said treating.

In some embodiments, the increase in VABS adaptive behavior composite score is at least about 1%, at least about 5%, at least about 10%, at least about 15%, at least about 20%, at least about 25%, at least about 30%, at least about 35%, at least about 40%, at least about 45%, at least about 50%, at least about 55%, or at least about 60% compared to prior to said treating.

In some embodiments, after said treatment the patient experiences an increase in sociability that is characterized by an increase in the VABS adaptive behavior socialization domain score compared to prior to the treatment. In some embodiments, the increase in the VABS adaptive behavior socialization domain score is about 1 point, about 2 points, about 3 points, about 4 points, about 5 points, about 6 points, about 7 points, about 8 points, about 9 points, about 10 points, about 11 points, about 12 points, about 13 points, about 14 points, about 15 points, about 16 points, about 17 points, about 18 points, about 19 points, about 20 points, about 21 points, about 22 points, about 23 points, about 24 points, about 25 points, about 26 points, about 27 points, about 28 points, about 29 points, about 30 points, about 31 points, about 32 points, about 33 points, about 34 points, about 35 points, about 36 points, about 37 points, about 38 points, about 39 points, about 40 points, about 41 points, about 42 points, about 43 points, about 44 points, about 45 points, about 46 points, about 47 points, about 48 points, about 49 points, about 50 points, about 51 points, about 52 points, about 53 points, about 54 points, about 55 points, about 56 points, about 57 points, about 58 points, about 59 points, about 60 points, about 61 points, about 62 points, about 63 points, about 64 points, about 65 points, about 66 points, about 67 points, about 68 points, about 69 points, or about 70 points compared to prior to said treating.

In some embodiments, the increase in VABS adaptive behavior socialization domain score is at least about 1%, at least about 5%, at least about 10%, at least about 15%, at least about 20%, at least about 25%, at least about 30%, at least about 35%, at least about 40%, at least about 45%, at least about 50%, at least about 55%, or at least about 60%, compared to prior to said treating. In some embodiments, the patient experiences an at least 10% improvement on the socialization domain score of VABS after treatment. In some embodiments, the patient experiences an at least 35% improvement on the socialization domain score of VABS after treatment.

In some embodiments, after said treatment the patient experiences an improvement in communication that is characterized by an increase in the VABS adaptive behavior communication domain score compared to prior to the treatment. In some embodiments, the increase in the VABS adaptive behavior communication domain is about 1 point, about 2 points, about 3 points, about 4 points, about 5 points, about 6 points, about 7 points, about 8 points, about 9 points, about 10 points, about 11 points, about 12 points, about 13 points, about 14 points, about 15 points, about 16 points, about 17 points, about 18 points, about 19 points, about 20 points, about 21 points, about 22 points, about 23 points, about 24 points, about 25 points, about 26 points, about 27 points, about 28 points, about 29 points, about 30 points, about 31 points, about 32 points, about 33 points, about 34 points, about 35 points, about 36 points, about 37 points, about 38 points, about 39 points, about 40 points, about 41 points, about 42 points, about 43 points, about 44 points, about 45 points, about 46 points, about 47 points, about 48 points, about 49 points, about 50 points, about 51 points, about 52 points, about 53 points, about 54 points, about 55 points, about 56 points, about 57 points, about 58 points, about 59 points, about 60 points, about 61 points, about 62 points, about 63 points, about 64 points, about 65 points, about 66 points, about 67 points, about 68 points, about 69 points, or about 70 points, compared to prior to the treatment.

In some embodiments, the increase in VABS adaptive behavior communication domain score is at least about 1%, at least about 5%, at least about 10%, at least about 15%, at least about 20%, at least about 25%, at least about 30%, at least about 35%, at least about 40%, at least about 45%, at least about 50%, at least about 55%, or at least about 60% compared to prior to said treating.

In some embodiments, efficacy of treatment according to the methods of the disclosure is determined by measuring the change in the Wechscler Adult Intelligence Scale, fourth edition (WAIS-IV) score by subtest. The Wechsler Adult Intelligence Scale (WAIS-IV) is an IQ test designed to measure intelligence and cognitive ability in adults and older adolescents. In some embodiments, after treating according to the methods of the disclosure, the Weschsler Intelligence Scale for Children shows an improvement by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% in an adult or older adolescent's intellectual ability. In some embodiments, efficacy of treatment according to the methods of the disclosure is determined by measuring the change in the Weschsler Preschool and Primary Scale of Intelligence. In some embodiments, the composite score after treating according to the methods of the disclosure increases. In some embodiments, the composite score after treating according to the methods of the disclosure increases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, including all values and ranges in between. In some embodiments, efficacy of treatment according to the methods of the disclosure is determined by measuring the change in the Weschsler Intelligence Scale for Children. In some embodiments, after treating according to the methods of the disclosure, the Weschsler Intelligence Scale for Children shows an improvement by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% in a child's intellectual ability.

In some embodiments, efficacy of treatment according to the methods of the disclosure is determined by measuring the change in the aberrant behavior checklist score. The aberrant behavior checklist (ABC) is a behavior rating scale that is utilized to rate individuals in five subscales: (1) irritability, agitation, and crying, (2) lethargy, social withdrawal, (3) stereotypic behavior, (4) hyperactivity and noncompliance, and (5) inappropriate speech. Individuals can be evaluated on the ABC by any adult that knows the individual well. The ABC contains a 58-item questionnaire that is utilized to assess the five-subscales. Each item on the 58-item questionnaire is rated from 0 to 3. A score of 0 means an absence in symptom. A score of 3 means an individual experiences the symptom with high severity. Items within each subscale are added to obtain a subscale score. Possible subscale scores on the ABC range from 0 to 48 with higher subscores indicating behavioral impairment. In some embodiments, after treating according to the methods of the disclosure, the patient experiences a reduction of symptoms associated with TSC that is characterized by at least a one point decrease in the ABC irritability agitation and crying (ABC-I) subscore. In some embodiments, after said treatment the patient experiences a reduction in irritability that is characterized by a decrease in the ABC-I communication domain score compared to prior to the treatment.

In some embodiments, efficacy of treatment according to the methods of the disclosure is determined by measuring the change in social communication questionnaire score. TSC patients often have autism spectrum disorders (ASD). The social communication questionnaire is a tool used by physicians to screen patients with ASD. An individual's caregiver rates the verbal individual on a score of 0 to 39 or the non-verbal individual on a scale of 0 to 33. An individual that has ASD is characterized by a social communication questionnaire that is above 15. In some embodiments, after said treatment the patient experiences a reduction of symptoms associated with ASD that is characterized by an at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% decrease in the social communication questionnaire scale compared to prior to said treatment.

In some embodiments, efficacy of treatment according to the methods of the disclosure is determined by measuring changes in a patient's quality of life. In some embodiments, a change in the quality of life in childhood epilepsy (QOLCE) questionnaire is utilized to determine efficacy of the methods of the disclosure. The maximum QOLCE score is 100. Higher scores are correlated with improved quality of life. In some embodiments, the QOLCE score increases after treatment according to the methods of the disclosure by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, including all values and ranges in between. In some embodiments, efficacy of treatment according to the methods of the disclosure is evaluated using the Quality of Life in Epilepsy (QOLIE-31-P) score. In some embodiments, after treatment according to the methods of the disclosure, the QOLIE-31-P score decreases compared to prior to said treatment. In some embodiments, the QOLIE-31-P decreases by at least about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, including all values and ranges in between.

In some embodiments, a patient's quality of life is assessed using the physician global impression of change (PGIC) score. In some embodiments, patients are assigned a score of 1 to 7, where 1 means that a patient is very much improved, and 7 means that a patient's condition has worsened. In some embodiments, after treating according to the methods of the disclosure, the PGIC decreases by at least about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, including all values and ranges in between.

In some embodiments, efficacy of treatment according to the methods of the disclosure is determined by measuring the change in serum insulin-like growth factor-1 (IGF-1) levels. IGF-1 is released after activation of the mTOR pathway. In some embodiments, after treating according to the methods of the disclosure, IGF-1 is reduced compared to prior to said treatment by at least about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%.

In some embodiments, efficacy of treatment according to the methods of the disclosure is determined by evaluating a patient's risk for suicide using the Columbia-Suicide Severity Rating Scale (C-SSRS; 19+ Years or C-SSRS Children's (6-18 years) score.

In some embodiments, efficacy of treatment according to the methods of the disclosure is determined by measuring the number of inpatient hospitalizations due to epilepsy. In some embodiments, after treating according to the methods of the disclosure the number of inpatient hospitalizations for a patient decreases. In some embodiments, the number of inpatient hospitalizations decreases by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%.

Patient Populations

In some embodiments, the methods of this disclosure are utilized to treat patients with TSC.

More than half of patients with TSC also develop autism spectrum disorders (ASDs). In some embodiments, the methods of the disclosure are utilized to treat TSC patients that have ASDs.

In some embodiments, the methods of the disclosure are utilized to treat patients from age 0-80. In some embodiments, the methods of the present disclosure are utilized to treat patients from about age 0 to about age 22. In some embodiments, the patients are about 0 years old, about 1 year old, about 2 years old, about 3 years old, about 4 years old, about 5 years old, about 6 years old, about 7 years old, about 8 years old, about 9 years old, about 10 years old, about 11 years old, about 12 years old, about 13 years old, about 14 years old, about 15 years old, about 16 years old, about 17 years old, about 18 years old, about 19 years old, about 20 years old, about 21 years old, or about 22 years old.

In some embodiments, the patients are administered CBD and/or everolimus based on the patient's body surface area (BSA). In some embodiments, patients exhibit a BSA between about 0.25 and 2.5. In some embodiments, patients have a BSA of about 0.25, or about 0.30, or about 0.35, or about 0.40, or about 0.45, or about 0.50, or about 0.55, or about 0.60, or about 0.65, or about 0.70, or about 0.75, or about 0.80, or about 0.85, or about 0.90, or about 0.95, or about 1.0, or about 1.1, or about 1.2, or about 1.3, or about 1.4, or about 1.5, or about 1.6, or about 1.7, or about 1.8, or about 1.9, or about 2.0, or about 2.1, or about 2.2, or about 2.3, or about 2.3, or about 2.4, or about 2.5, or more, including all values and ranges in between. In some embodiments, a patient's body surface area is calculated according to the following formula: BSA=weight $(kg)^{0.425} \times$ height $(cm)^{0.725} \times 0.007184$. In some embodiments, a patient's body surface area is calculated according to the following formula:

$$BSA(m^2) = \sqrt{\frac{\text{(height (cm)} \times \text{weight (kg)}}{3600}}.$$

In some embodiments, the disclosure provides methods of coadministering everolimus and CBD (e.g., having a purity of at least 95% or 98% w/w) to treat TSC patients with moderate or severe hepatic impairment. In some embodiments, such patients may receive a lower starting dose, maintenance dose, and maximum dose compared to the dose and otherwise identical patient with moderate or severe hepatic impairment would receive in the absence of everolimus. Table 3 lists CBD doses for patients with moderate or severe hepatic impairment in the absence of everolimus.

TABLE 3

CBD Doses Patients with Hepatic Impairment

| Hepatic Impairment | Starting Dosage | Maximum Recommended Dosage |
|---|---|---|
| Mild | 2.5 mg/kg twice daily (5 mg/kg/day) | 12.5 mg/kg twice daily (25 mg/kg/day) |
| Moderate | 1.25 mg/kg twice daily (2.5 mg/kg/day) | 6.25 mg/kg twice daily (12.5 mg/kg/day) |
| Severe | 0.5 mg/kg twice daily (1 mg/kg/day) | 2.5 mg/kg twice daily (5 mg/kg/day) |

In some embodiments, a TSC patient with mild renal impairment is co-administered 2.5 or 5 mg everolimus, and a staring dose of CBD that is less than 5 mg/kg/day (e.g., about 1, about 2, about 3, about 4, or about 5 mg/kg/day). In some embodiments, the starting dose is increased by about 1 mg/kg/day to about 5 mg/kg/day (e.g., about 1, about 2, about 3, about 4, or about 5 mg/kg/day) up to a maximum dose of less than 25 mg/kg/day (e.g., about 24, about 23, about 22, about 21, about 20, about 19, about 18, about 17, about 16, about 15, about 14, about 13, about 12, about 11, about 10, about 9, about 8, about 7, about 6, about 5, mg/kg/day, including all values and ranges between these values). In some embodiments, patients with mild hepatic impairment are treated with a dose of CBD ranging from about 5 to about 20 mg/kg/day.

In some embodiments, a TSC patient with moderate renal impairment is co-administered 2.5 or 5 mg everolimus, and a staring dose of CBD that is less than 2.5 mg/kg/day (e.g., about 0.5 mg/kg/day, or about 1 mg/kg/day). In some embodiments, the starting dose is increased by about 0.5 mg/kg/day to about 2.5 mg/kg/day (e.g., about 0.5, about 1, about 1.5 or about 2 mg/kg/day) up to a maximum dose of less than 12.5 mg/kg/day (e.g., about 12, about 11, about 10, about 9, about 8, about 7, about 6, about 5, about 4, about 3, about 2.5 mg/kg/day, including all values and ranges between these values). In some embodiments, patients with moderate hepatic impairment are treated with a dose of CBD ranging from about 2.5 to about 10 mg/kg/day.

In some embodiments, a TSC patient with severe renal impairment is co-administered 2.5 or 5 mg everolimus, and a staring dose of CBD that is less than 1 mg/kg/day (e.g., about 0.25, mg/kg/day, or about 0.5 mg/kg/day). In some embodiments, the starting dose is increased by about 0.5 mg/kg/day up to a maximum dose of less than 5 mgkg/day (e.g., about 0.5, about 1, about 1.5, about 2, about 2.5, about 3, about 3.5, about 4, or 4.5 mg/kg/day).

In some embodiments, the patent had a diagnosis of TSC and the seizures were inadequately controlled with at least one concomitant anti-epileptic drug (AED), with or without vagal nerve stimulation or ketogenic diet. In some embodiments, the AED is valproate, vigabatrin, levetiracetam, clobazam, or combinations thereof.

EXAMPLES

Example 1. Preparation of a CBD Extract

A highly purified (>98% w/w CBD) cannabidiol extract was prepared for treatment of TSC patients. The production of this extract is also described in U.S. Pat. No. 10,111,840 and U.S. Patent App. Pub. No. 2016/0166514, each of which are incorporated by reference herein in its entirety.

Summary: CBD was extracted from high-CBD containing chemotypes of *Cannabis sativa* L. using a liquid carbon dioxide extraction method. The CBD extract was further purified using a solvent crystallization method to yield CBD. The crystallization method specifically removes other cannabinoids to yield a CBD extract that contains greater than 95% w/w CBD and typically greater than 98% w/w CBD.

Procedure: The *Cannabis sativa* L. plants are grown, harvested, and processed to make a botanical extract (intermediate). The plant starting material is referred to as Botanical Raw Material (BRM). The active pharmaceutical ingredient (API), also called drug substance, is CBD.

The BRM and botanical extract (intermediate) are controlled by the specifications. The drug substance specification is described in Table 4.

The purity of the CBD drug substance achieved is greater than 98%. The other cannabinoids which may occur in the extract are: CBDA, CBDV, CBD-C4 and THC.

Distinct chemotypes of *Cannabis sativa* L. plant have been produced to maximize the output of the specific chemical constituents, the cannabinoids. One type of plant produces predominantly CBD. Only the (−)-trans isomer occurs naturally, furthermore during purification the stereochemistry of CBD is not affected.

An overview of the steps to produce a botanical extract, the intermediate, are as follows:
  (i) Growing
  (ii) Decarboxylation
  (iii) Extraction Number 1: Using liquid $CO_2$
  (iv) Extraction Number 2: "Winterization" using ethanol
  (v) Filtration
  (vi) Evaporation High CBD chemovars were grown, harvested and dried and stored in a dry room until required. The botanical raw material (BRM) was finely chopped using an Apex mill fitted with a 1 mm screen. The milled BRM was stored in a freezer for up to 3 months prior to extraction. Decarboxylation of CBDA to CBD was carried out using a large Heraeus tray oven. The decarboxylation batch size in the Heraeus is approximately 15 Kg. Trays were placed in the oven and heated to 105° C.; the BRM took 96.25 minutes to reach 105° C. Held at 105° C. for 15 Minutes. Oven then set to 150° C.; the BRM took 75.7 minutes to reach 150° C.; BRM held at 150° C. for 130 Minutes. Total time in the oven was 380 Minutes, including 45 minutes cooling and 15 Minutes venting.

TABLE 4

| CBD Specification | | |
|---|---|---|
| Test | Test Method | Limits |
| Apperance | Visual | Off-white/pale yellow crystals |
| Identification A | HPLC-UV | Retention time of major peak corresponds to certified CBD reference standard |
| Identification B | GC-FID/MS | Retention time and mass spectrum of major peak corresponds to certified CBD reference standard |
| Identification C | FT-IR | Conforms to reference spectrum for certified CBD reference standard |
| Identification D | Melting Point | 65° C. to 67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | High Performance Liquid Chromatography - Ultraviolet (UV) | ≥98.0% |
| Chromatographic Purity 2 | Gas Chromatography-flame ionization detector/mass spectrometry (GC-FID/MS) | ≥98.0% |
| CBDA | High Performance Liquid Chromatography - UV | Not more than 0.15% w/w |
| CBDV | High Performance Liquid Chromatography - UV | Not more than 1.0% w/w |
| $\Delta^9$THC | High Performance Liquid Chromatography - UV | Not more than 0.15% w/w |
| CBD-C4 | High Performance Liquid Chromatography - UV | Not more than 0.5% w/w |
| Alkane | Gas chromatography | Not more than 0.5% w/w |
| Ethanol | Gas chromatography | Not more than 0.5% w/w |
| Residual Water | Karl Fischer | Not more than 1.0% w/w |

Extraction Number 1 was performed using liquid $CO_2$ at 60 bar/10° C. to produce botanical drug substance (BDS) which was used for crystallisation to produce the test material.

The crude CBD BDS was winterized in Extraction Number 2 under standard conditions (two volumes of ethanol at minus 20° C. for around 50 hours). The precipitated waxes were removed by filtration.

The manufacturing steps to produce the drug substance (CBD) from the intermediate botanical extract are as follows:
(i) Crystallization using C5-C12 straight chain or branched alkane
(ii) Filtration
(iii) Optional recrystallization from C5-C12 straight chain or branched alkane
(iv) Vacuum Drying Intermediate botanical extract (12 kg) produced using the methodology above was dispersed in C5-C12 straight chain or branched alkane (9000 ml, 0.75 vols) in a 30 liter stainless steel vessel. The mixture was manually agitated to break up any lumps and the sealed container then placed in a freezer for approximately 48 hours.

The crystals were isolated by vacuum filtration, washed with aliquots of cold C5-
C12 straight chain or branched alkane (total 12000 ml), and dried under a vacuum of <10 mb at a temperature of 60° C. until dry before submitting the drug substance for analysis. The dried product was stored in a freezer at minus 20° c. in a pharmaceutical grade stainless steel container, with FDA food grade approved silicone seal and clamps.

The drug product is presented as an oral solution containing the drug substance. The oral solution presentation contains 25 mg/ml or 100 mg/ml CBD, with the excipients sesame oil, ethanol, sucralose and flavoring. Two product strengths are available to allow dose titration across a wide dose range. The 25 mg/ml solution is appropriate at lower doses and the 100 mg/ml solution at higher doses.

The drug product is described in Table 5 below.

TABLE 5

Drug Product Specification

| Component | Qualitative Composition | Function | Reference to Quality Standard |
| --- | --- | --- | --- |
| Cannabidiol (CBD) | 25 mg/mL or 100 mg/mL | Active Ingredient | In-house |
| Anhydrous Ethanol | 79.0 mg/mL | Excipient | Ph.Eur. |
| Sucralose | 0.5 mg/mL | Sweetener | In-house |
| Strawberry flavoring | 0.2 mg/mL | Flavoring | In-house |
| Sesame Oil | q.s. to 1.0 mL | Excipient | Ph.Eur. |

The drug substance CBD is insoluble in water. Sesame oil was selected as an excipient to solubilize the drug substance. A sweetener and fruit flavoring are required to improve palatability of the sesame oil solution. Ethanol was required to solubilize the sweetener and the flavoring. The composition can be substantially equivalent, by which is meant that the function ingredients can vary from the qualitative composition specified in Table 6 by an amount up to 10%.

Example 2. Inhibition of CYP450 by CBD

In vitro studies were performed to measure CYP450 inhibition by CBD. CBD has an $IC_{50}=1.42$ μM against CYP3A4-mediated testosterone hydroxylation. CBD also has a $K_1=1.5$ μM against CYP3A4-mediated testosterone hydroxylation, $K_{inact}=0.14$ min'.

The in vitro data shows that CBD has the potential to inhibit multiple CYP450s in vivo.

While the in vitro data suggest that CBD may cause DDI with CYP3A4 substrates, clinical DDI study with midazolam (GWEP17028, herein incorporated by reference) showed no clinically significant effect on orally dosed midazolam PK parameters when dosed concomitantly with CBD at steady-state (750 mg bid, fed state).

Example 3. A Phase 1, Open-Label, Pharmacokinetic Drug-Drug Interaction Trial to Investigate the Effect of Cannabidiol on the Pharmacokinetics (PK) of Everolimus Rationale: Everolimus is an mTOR inhibitor approved as an oral treatment in patients with tuberous sclerosis complex (TSC) to manage TSC associated-seizures, where it may be used concomitantly with CBD. Nonclinical ADME data show that there is potential for CBD to interact with the pathways involved in the absorption and elimination of everolimus. The principal aim of this trial was to assess the effects that CBD has on the pharmacokinetic (PK) parameters of everolimus.

Primary Objectives: To investigate the effect of CBD treatment following repeated dosing on the PK of a single dose of everolimus in healthy participants.

Primary Endpoints: The PK parameter endpoints, derived from the plasma concentration-time profiles of everolimus on Day 1 administered alone and the PK parameter endpoints derived from a single dose of everolimus in participants at steady state CBD following 5 days of CBD, 12.5 mg/kg twice daily (b.i.d).

Secondary Objectives: To evaluate the safety and tolerability of CBD when given with a single dose of everolimus in healthy participants; to investigate the effect of a single everolimus dose on the PK parameters of CBD at steady state in healthy participants Secondary Endpoints: Safety includes: incidence and severity of adverse events (AEs), incidence of laboratory abnormalities based on hematology, clinical chemistry, and urinalysis test results; 12-lead electrocardiogram (ECG) parameters, vital sign measurements, physical examinations, Columbia-Suicide Severity Rating Scale (C-SSRS) questionnaire scores; the PK parameter endpoints, derived from the plasma concentration-time profiles of everolimus on Day 1 administered alone and the PK parameter endpoints derived from a single dose of everolimus in participants at steady state CBD following 5 days of CBD, 12.5 mg/kg twice daily (b.i.d) (total daily dose of 25 mg/kg/day).

Exploratory Objectives: To investigate potential effects of CYP3A genotypes on everolimus exposure and any interaction with CBD.

Exploratory Endpoints: pharmacogenetic assessment of common genetic variants in CYP3A enzymes (this information may be correlated with PK outcomes)

Design: This was a phase 1, open-label, single site trial to investigate the effect of multiple dose administration of CBD on the PK of everolimus in healthy participants. The duration of the trial was approximately 9 weeks, which includes a screening period (up to 4 weeks), a treatment period (18 days) and a safety follow-up period (2 weeks). After signing the informed consent form (ICF), participants enter the screening period (Day −28 to −1). On Day −1, screened participants who continued to meet eligibility criteria were admitted to the clinical research unit (CRU) at approximately 2 pm and enrolled into the trial. On Day 1, participants received everolimus, 30 minutes after starting a standard meal. On Days 2 to 8, participants had a 7-day washout period. On Days 9 to 12, participants received CBD, 30 minutes after starting a standard meal. On Day 13, participants received everolimus and CBD, 30 minutes after starting a standard meal. On Days 14 to 18, participants received CBD, 30 minutes after starting a standard meal. On Day 18, participants were discharged from the CRU once all assessments were completed. On Day 32, a safety follow-up visit was conducted 14 days (±3 days) after the last dose of investigational medicinal product (IMP), CBD.

During the initial trial, patients received 5 mg everolimus and 12.5 mg/kg CBD b.i.d. (total daily dose of 25 mg/kg/day).

Many doses of CBD and everolimus are tested according to the study design outlined above, as shown in Table 6. CBD is administered twice daily at the doses listed in Table 6.

TABLE 6

Potential Doses of CBD (b.i.d.) and everolimus

| Everolimus | CBD |
|---|---|
| 2.0 mg | 2.5 mg/kg |
| 2.0 mg | 5 mg/kg |
| 2.0 mg | 10 mg/kg |
| 2.0 mg | 12.5 mg/kg |
| 2.5 mg | 2.5 mg/kg |
| 2.5 mg | 5 mg/kg |
| 2.5 mg | 10 mg/kg |
| 2.5 mg | 12.5 mg/kg |
| 5 mg | 2.5 mg/kg |
| 5 mg | 5 mg/kg |
| 5 mg | 10 mg/kg |
| 5 mg | 12.5 mg/kg |
| 10 mg | 2.5 mg/kg |
| 10 mg | 5 mg/kg |
| 10 mg | 10 mg/kg |
| 10 mg | 12.5 mg/kg |
| 4.5 mg/m$^2$ | 2.5 mg/kg |
| 4.5 mg/m$^2$ | 5 mg/kg |
| 4.5 mg/m$^2$ | 10 mg/kg |
| 4.5 mg/m$^2$ | 12.5 mg/kg |
| 2.25 mg/m$^2$ | 2.5 mg/kg |
| 2.25 mg/m$^2$ | 5 mg/kg |
| 2.25 mg/m$^2$ | 10 mg/kg |
| 2.25 mg/m$^2$ | 12.5 mg/kg |
| 5.0 mg/m$^2$ | 2.5 mg/kg |
| 5.0 mg/m$^2$ | 5 mg/kg |
| 5.0 mg/m$^2$ | 10 mg/kg |
| 5.0 mg/m$^2$ | 12.5 mg/kg |
| 2.5 mg/m$^2$ | 2.5 mg/kg |
| 2.5 mg/m$^2$ | 5 mg/kg |
| 2.5 mg/m$^2$ | 10 mg/kg |
| 2.5 mg/m$^2$ | 12.5 mg/kg |

Formulation Mode of Administration, Dose, Regimen: The BCD formulation is an oral liquid formulation that is clear and colorless to yellow in appearance (100 mg/mL CBD in sesame oil with anhydrous ethanol, added sweetener (sucralose), and strawberry flavoring. The oral liquid formulation is administered with a syringe. The CBD formulation was taken b.i.d. 30 minutes after starting a standard meal Everolimus was taken by mouth (p.o) 30 minutes after a standard meal.

Procedures: All visits were scheduled to take place at approximately the same time of day (i.e., morning or afternoon), whenever possible. *Cannabis* or benzodiazepines will not be allowed throughout the trial. Alcohol was not allowed from 48 hours prior to each admission to the CRU and throughout the inpatient period, and from 48 hours prior to the safety follow-up visit.

Pharmacokinetic Assessments: PK blood sampling was collected for everolimus and CBD, 7-hydroxy-cannabidiol (7-OH-CBD) and 7-carboxy-cannabidiol (7-COOH-CBD) and were collected during the treatment period at the timepoints listed in the Schedule of Assessments. The time of the meal consumed at the site during days of IMP administration was recorded, as was the dose and dosing time of IMP (as appropriate) relative to sampling times.

The following assessments were performed: demographics, medical history, physical examination, vital signs, body weight, height, 12-lead ECG, adverse events (AEs), previous and concomitant medications recorded. The investigator or delegate completes the C-SSRS. Clinical laboratory samples including chemistry, hematology, serology, urine drug screen, alcohol test, and pharmacogenetics.

Treatment Period Assessments: Participants who continued to satisfy all inclusion criteria and none of the exclusion criteria, were enrolled to receive everolimus and CBD. The following assessments were performed: physical examination, vital signs, 12-lead ECG, concomitant medications recorded, and AEs are reviewed. The investigator or delegate completes the C-SSRS. Clinical laboratory samples including chemistry, coagulation, hematology, and samples for PK analysis.

Safety Follow-Up Visit Assessments: The following assessments were performed: physical examination, vital signs, 12-lead ECG, adverse events (AEs), and concomitant medications recorded. The investigator or delegate completed the C-SSRS. Clinical laboratory samples including chemistry and hematology.

Pharmacokinetic parameter estimates were evaluated to assess the change in PK parameters of CBD, 7-OH-CBD and 7-COOH-CBD at steady state CBD, following a single dose of everolimus.

Log transformed $C_{max}$, $AUC_{(0-\infty)}$, and $AUC_{(0-t)}$ parameters for everolimus were analyzed using a linear mixed-effects model with a fixed effect for treatment and a random effect for participant. The treatment differences are back transformed to present the ratios of geometric means and the corresponding 90% confidence intervals (CIs).

For $t_{max}$, nonparametric analysis of the same comparisons were performed using a Wilcoxon signed-rank test. Medians and median differences between the treatments were presented along with the approximate 90% CI for the median difference.

Geometric mean ratios and 90% CIs were used to estimate the magnitude of any interaction and will be interpreted based on clinical relevance.

$C_{trough}$ values for CBD, 7-OH-CBD and 7-COOH-CBD are listed and summarized as appropriate.

All AEs are listed and summarized using descriptive methodology. The incidence of AEs for each treatment period are presented by severity and by association with the IMPs as determined by the Investigator (or designee). All safety data is listed and summarized using a descriptive methodology. Pharmacogenetic data will be listed.

Results:

Initially, patients received 5 mg everolimus, or 5 mg everolimus and 12.5 mg/kg CBD b.i.d. (total daily dose of 25 mg/kg/day) according to the trial design described above. See FIG. 1. 5 mg everolimus and 25 mg/kg/day CBD represent the dose of everolimus and CBD, respectively, that TSC patients would receive based on the current FDA labels.

Figure 2:
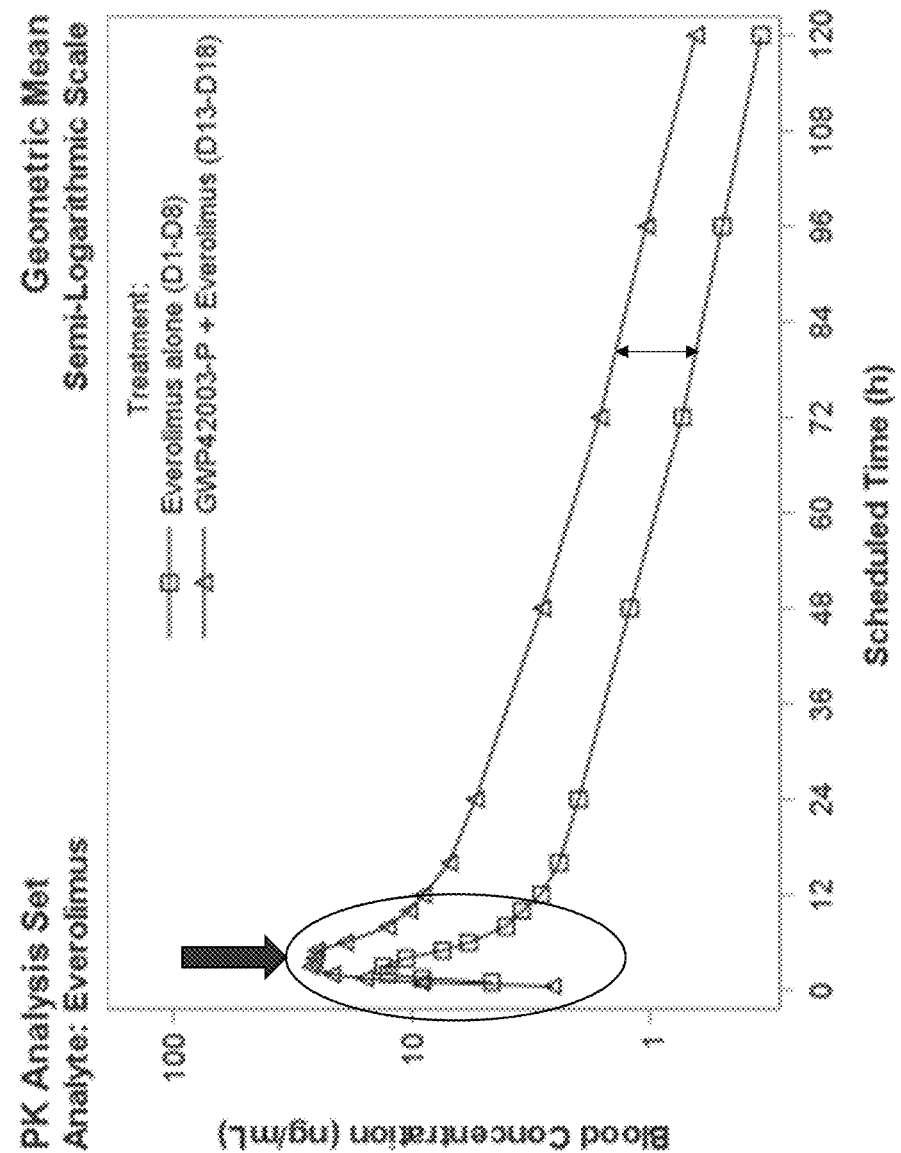
FIG. 2 shows the blood concentration profile (ng/mL) of everolimus in patients that received everolimus alone, and patients that received both everolimus and CBD.

The blood plasma concentration profiles of everolimus and CBD were measured the time points described above. FIG. 2 shows the blood concentration profile (ng/mL) of everolimus in patients that received everolimus alone, and patients that received both everolimus and CBD. As shown in FIG. 2, CBD surprisingly and unexpectedly causes elevations in the blood plasma concentrations of everolimus, even though CBD was not considered to be moderate or strong CYP3A4 and P-gp inhibitor. The results are summarized in Table 7.

TABLE 7

Analysis of Drug-Drug Interaction PK Everolimus (EVE)

| | | Geometric LS means | | Ratio Test/Reference | | |
|---|---|---|---|---|---|---|
| Analyte | PK Parameter | EVE Alone (n = 16) | EVE + CBD (n = 16) | Estimate | 91% CI (lower, upper) | P value |
| Everolimus | Cmax (ng/mL) | 18 | 46 | 2.5 | (2.12, 2.94) | <0.0001 |
| | $AUC_{0-last}$ (h*ng/mL) | 95 | 497 | 2.55 | (2.23, 2.90) | <0.0001 |
| | $AUC_{0-inf}$ (h*ng/mL) | 216 | 529 | 2.45 | (2.15, 2.80) | <0.0001 |

As shown above in Table 7 and FIG. 2, CBD (at SS) increased the Cmax and AUC of everolimus by at least 2.5-fold. This is a clinically significant, moderate interaction (Clinical Drug Interaction Studies—Cytochrome P450 Enzyme- and Transporter-Mediated Drug Interactions Guidance for Industry, FDA, January 2020). Consequently, the dose of CBD was reduced (e.g., as described herein) to mitigate the DDI with everolimus.

Figure 3:
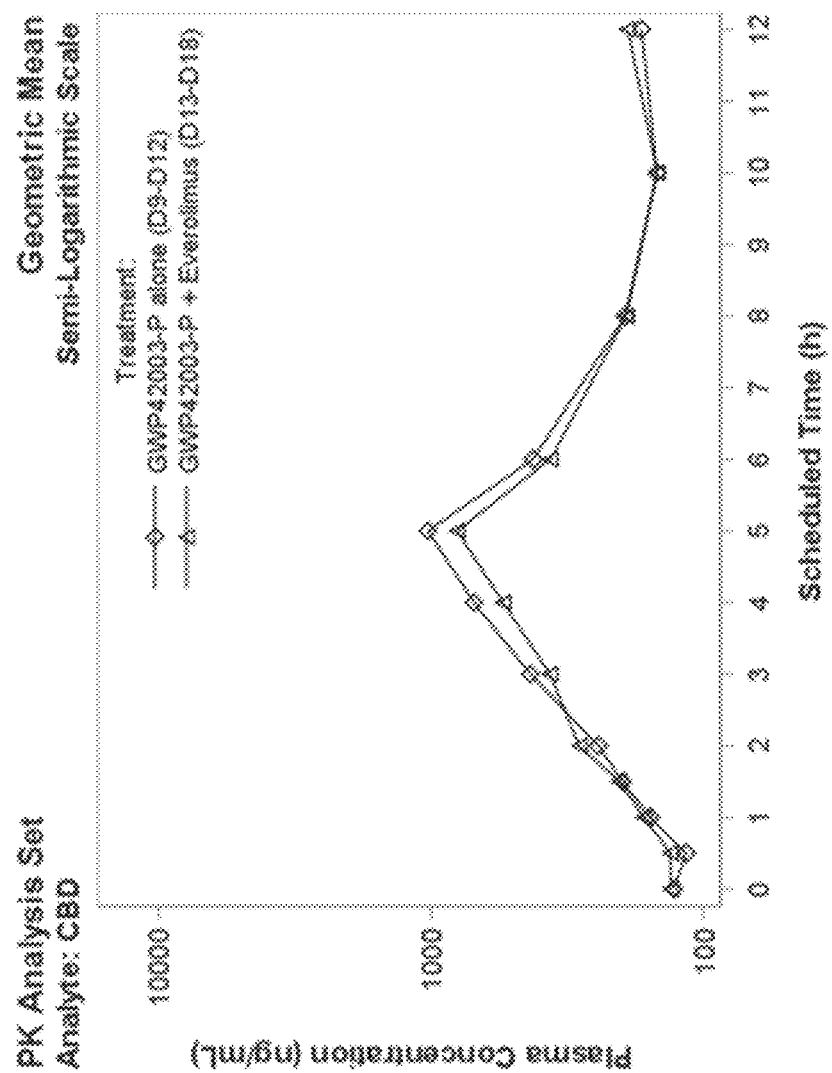
FIG. 3 shows the blood concentration profile (ng/mL) of CBD in patients that received CBD alone, and patients that received both everolimus and CBD.
Figure 4:
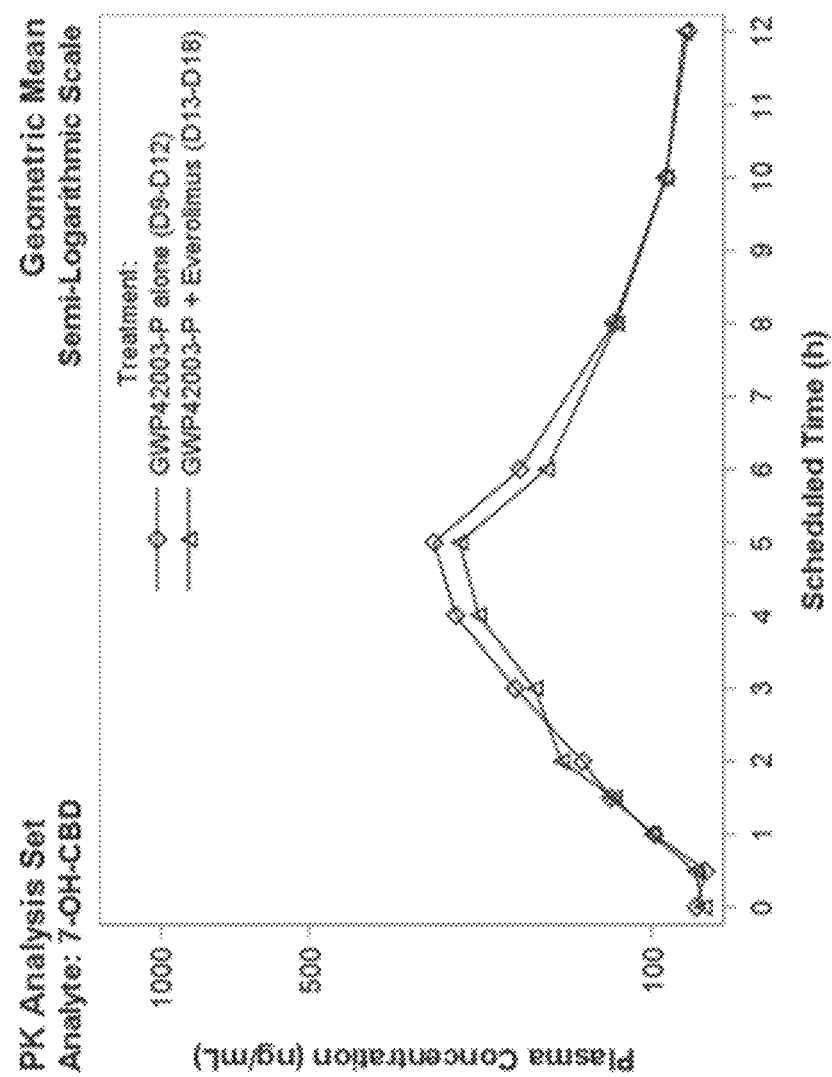
FIG. 4 shows the blood concentration profile (ng/mL) of 1-OH-CBD in patients that received CBD alone, and patients that received both everolimus and CBD.
Figure 5:
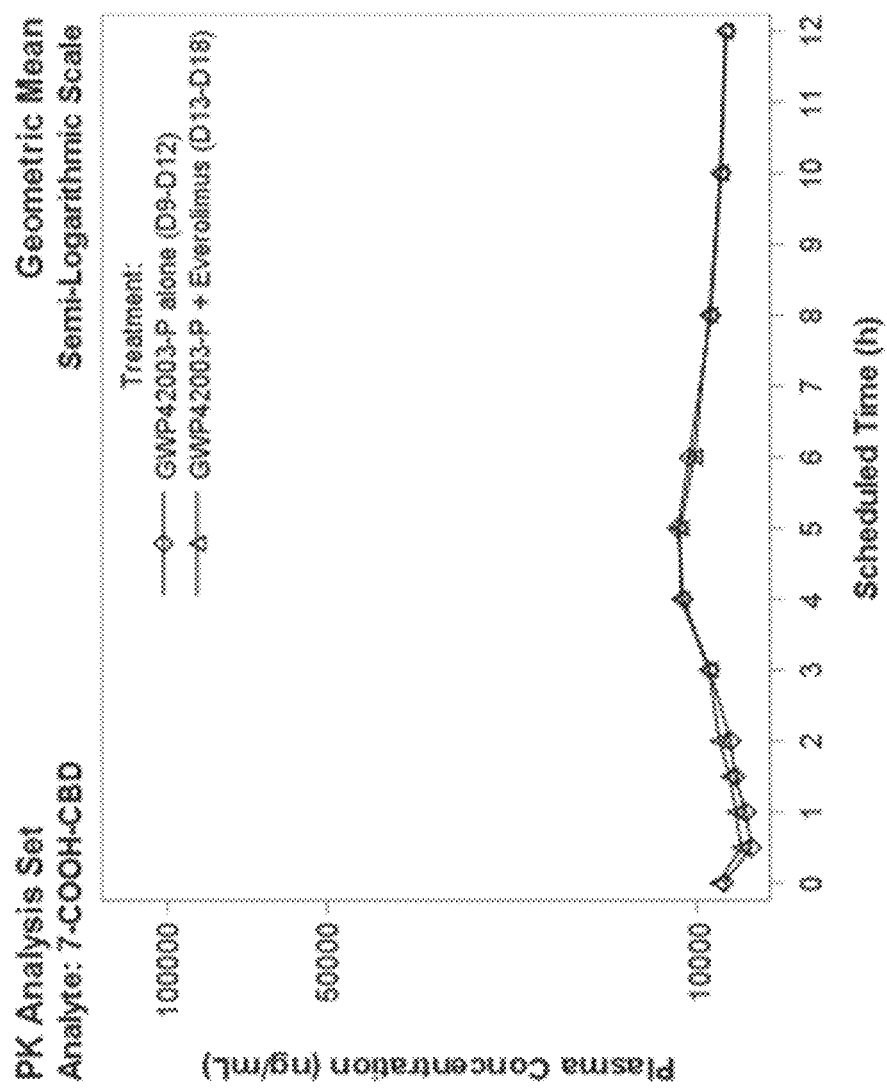
FIG. 5 shows the blood concentration profile (ng/mL) of 1-COOH-CBD in patients that received CBD alone, and patients that received both everolimus and CBD.

FIG. 3-5 shows that everolimus did not have a clinical significant impact of the pharmacokinetics of CBD, or its metaboliates 7-OH-CBD, and 7-COOH-CBD, respectively.

As noted above, the CBD (at SS) increased the Cmax and AUC of everolimus by at least 2.5-fold. In order to mitigate the impact of CBD on everlimus blood plasma concentration, and reduce the risk of side effects related to everolimus overexposure, the dose of CBD administered to TSC is reduced as described herein. It is important to note that reducing the CBD dose by 2.5 fold is not required to safely and effectively co-administer everolimus and CBD (although a 2.5 fold reduction in the CBD is encompassed by this disclosure). In some embodiments, the CBD dose need only be reduce enough such that the everolimus AUC (or Cmax) is increased by no more than 2 fold. Without being bound by theory, this can be achieved by administering 20 mg/kg/day CBD in combination with everolimus, as less than 2 fold increases in everolimus AUC (or Cmax) are not considered clinically relevant.

In another example, to mitigate the impact of CBD on everlimus blood plasma concentration, and reduce the risk of side effects related to everolimus overexposure, the dose of everolimus is reduced as described herein. It is important to note that reducing the everolimus dose by 2.5 fold is not required to safely and effectively co-administer everolimus and CBD (although a 2.5 fold reduction in the CBD is encompassed by this disclosure). In some embodiments, the CBD dose need only be reduce enough such that the everolimus AUC (or Cmax) is increased by no more than 2 fold. Without being bound by theory, this can be achieved by reducing the everolimus dose by 10%, 15%, 20%, and/or 25%.

NUMBERED EMBODIMENTS OF THE DISCLOSURE

Notwithstanding the appended claims, the disclosure sets forth the following numbered embodiments:

Embodiment 1. A method of treating seizures associated with tuberous sclerosis complex (TSC) in a patient in need thereof, comprising administering everolimus in combination with a reduced dose of cannabidiol (CBD).

Embodiment 2. The method of embodiment 1, wherein the reference dose of CBD is 25 mg/kg/day, and the patient is administered 2.5 mg of everolimus, and the reduced dose of CBD is selected from the group consisting of about 5 mg/kg/day, about 10 mg/kg/day, about 15 mg/kg/day, and about 20 mg/kg/day.

Embodiment 3. The method of embodiment 1 or 2, wherein the reference dose of CBD is 25 mg/kg/day, and the patient is administered 2.5 mg of everolimus, and the reduced dose of CBD is about 5 mg/kg/day.

Embodiment 4. The method of embodiment 1 or 2, wherein the reference dose of CBD is 25 mg/kg/day, and the patient is administered 2.5 mg of everolimus, and the reduced dose of CBD is about 10 mg/kg/day.

Embodiment 5. The method of embodiment 1 or 2, wherein the reference dose of CBD is 25 mg/kg/day, and the patient is administered 2.5 mg of everolimus, and the reduced dose of CBD is about 15 mg/kg/day.

Embodiment 6. The method of embodiment 1 or 2, wherein the reference dose of CBD is 25 mg/kg/day, and the patient is administered 2.5 mg of everolimus, and the reduced dose of CBD is about 20 mg/kg/day.

Embodiment 7. The method of embodiment 1, wherein the reference dose of CBD is 20 mg/kg/day, and the patient is administered 2.5 mg of everolimus, and the reduced dose of CBD is selected from the group consisting of about 5 mg/kg/day, about 10 mg/kg/day, and about 15 mg/kg/day.

Embodiment 8. The method of embodiment 1 or 7, wherein the reference dose of CBD is 20 mg/kg/day, and the patient is administered 2.5 mg of everolimus, and the reduced dose of CBD is about 5 mg/kg/day.

Embodiment 9. The method of embodiment 1 or 7, wherein the reference dose of CBD is 20 mg/kg/day, and the patient is administered 2.5 mg of everolimus, and the reduced dose of CBD is about 10 mg/kg/day.

Embodiment 10. The method of embodiment 1 or 7, wherein the reference dose of CBD is 20 mg/kg/day, and the patient is administered 2.5 mg of everolimus, and the reduced dose of CBD is about 15 mg/kg/day.

Embodiment 11. The method of embodiment 1, wherein the reference dose of CBD is 15 mg/kg/day, and the patient is administered 2.5 mg of everolimus, and the reduced dose of CBD is selected from the group consisting of about 5 mg/kg/day, and about 10 mg/kg/day.

Embodiment 12. The method of embodiment 1 or 11, wherein the reference dose of CBD is 15 mg/kg/day, and the patient is administered 2.5 mg of everolimus, and the reduced dose of CBD is about 5 mg/kg/day.

Embodiment 13. The method of embodiment 1 or 11, wherein the reference dose of CBD is 25 mg/kg/day, and the patient is administered 2.5 mg of everolimus, and the reduced dose of CBD is about 10 mg/kg/day.

Embodiment 14. The method of embodiment 1 or 7, wherein the reference dose of CBD is 10 mg/kg/day, and the patient is administered 2.5 mg of everolimus, and the reduced dose of CBD is about 5 mg/kg/day.

Embodiment 15. The method of embodiment 1, wherein the reference dose of CBD is 25 mg/kg/day, and the patient is administered 5 mg of everolimus, and the reduced dose of CBD is selected from the group consisting of about 5 mg/kg/day, about 10 mg/kg/day, about 15 mg/kg/day, and about 20 mg/kg/day.

Embodiment 16. The method of embodiment 1 or 15, wherein the reference dose of CBD is 25 mg/kg/day, and the patient is administered 5 mg of everolimus, and the reduced dose of CBD is about 5 mg/kg/day.

Embodiment 17. The method of embodiment 1 or 15, wherein the reference dose of CBD is 25 mg/kg/day, and the patient is administered 5 mg of everolimus, and the reduced dose of CBD is about 10 mg/kg/day.

Embodiment 18. The method of embodiment 1 or 15, wherein the reference dose of CBD is 25 mg/kg/day, and the patient is administered 5 mg of everolimus, and the reduced dose of CBD is about 15 mg/kg/day.

Embodiment 19. The method of embodiment 1 or 15, wherein the reference dose of CBD is 25 mg/kg/day, and the patient is administered 5 mg of everolimus, and the reduced dose of CBD is about 20 mg/kg/day.

Embodiment 20. The method of embodiment 1, wherein the reference dose of CBD is 20 mg/kg/day, and the patient is administered 5 mg of everolimus, and the reduced dose of CBD is selected from the group consisting of about 5 mg/kg/day, about 10 mg/kg/day, and about 15 mg/kg/day.

Embodiment 21. The method of embodiment 1 or 20, wherein the reference dose of CBD is 20 mg/kg/day, and the patient is administered 5 mg of everolimus, and the reduced dose of CBD is about 5 mg/kg/day.

Embodiment 22. The method of embodiment 1 or 20, wherein the reference dose of CBD is 20 mg/kg/day, and the patient is administered 5 mg of everolimus, and the reduced dose of CBD is about 10 mg/kg/day.

Embodiment 23. The method of embodiment 1 or 20, wherein the reference dose of CBD is 20 mg/kg/day, and the patient is administered 5 mg of everolimus, and the reduced dose of CBD is about 15 mg/kg/day.

Embodiment 24. The method of embodiment 1, wherein the reference dose of CBD is 15 mg/kg/day, and the patient is administered 5 mg of everolimus, and the reduced dose of CBD is selected from the group consisting of about 5 mg/kg/day, and about 10 mg/kg/day.

Embodiment 25. The method of embodiment 1 or 24, wherein the reference dose of CBD is 15 mg/kg/day, and the patient is administered 5 mg of everolimus, and the reduced dose of CBD is about 5 mg/kg/day.

Embodiment 26. The method of embodiment 1 or 24, wherein the reference dose of CBD is 25 mg/kg/day, and the patient is administered 5 mg of everolimus, and the reduced dose of CBD is about 10 mg/kg/day.

Embodiment 27. The method of embodiment 1 or 15, wherein the reference dose of CBD is 10 mg/kg/day, and the patient is administered 5 mg of everolimus, and the reduced dose of CBD is about 5 mg/kg/day.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

The invention claimed is:

1. A method of initiating everolimus treatment in a human who is suffering from tuberous sclerosis complex and has partial onset seizures who is currently being treated with a therapeutically effective amount of cannabidiol, the method comprising:
   (a) co-administering a reduced starting dose of everolimus and the therapeutically effective amount of cannabidiol to the human;
   (b) monitoring the human's blood plasma concentration of everolimus;
   (c) increasing the reduced starting dose of everolimus administered in step (a) by at least 10% to a dose that achieves a blood plasma trough concentration of everolimus ranging from 5-15 ng/mL, Cmax of everolimus that is less than or equal to 50 ng/mL, or $AUC_{0-24}$ of everolimus that is less than or equal to 500 h*ng/mL;
   wherein said monitoring in step (b) occurs one to two weeks after the human begins receiving everolimus;
   wherein cannabidiol is synthetic or purified; and
   wherein the starting dose of everolimus for treating tuberous sclerosis complex in the human is 5 mg/m² once daily.

2. The method of claim 1, wherein the therapeutically effective amount of cannabidiol ranges from about 5 mg/kg/day to about 25 mg/kg/day.

3. The method of claim 1, wherein the therapeutically effective amount of cannabidiol is 25 mg/kg/day.

4. The method of claim 1, wherein the human has normal hepatic status or mild hepatic impairment, and the therapeutically effective amount of cannabidiol administered in step (a) is about 25 mg/kg/day.

5. The method of claim 1, wherein the human has moderate hepatic impairment, and the therapeutically effective amount of cannabidiol administered in step (a) is about 12.5 mg/kg/day.

6. The method of claim 1, wherein the human has severe hepatic impairment, and the therapeutically effective amount of cannabidiol administered in step (a) is about 5 mg/kg/day.

7. The method of claim 1, wherein the cannabidiol is purified.

8. The method of claim 7, wherein the cannabidiol has a purity of at least 95% (w/w) cannabidiol.

9. The method of claim 8, wherein the cannabidiol has a purity of at least 98% (w/w) cannabidiol.

10. The method of claim 1, wherein the reduced starting dose of everolimus administered in step (a) is less than 4.5 mg/m² of everolimus once daily.

11. The method of claim 1, wherein the reduced starting dose of everolimus administered in step (a) ranges from about 2.5 mg/m$^2$ to about 4.5 mg/m$^2$ of everolimus.

12. The method of claim 1, wherein the reduced starting dose of everolimus administered in step (a) is about 2.5 mg/m$^2$.

13. The method of claim 1, wherein the reduced starting dose of everolimus administered in step (a) ranges from about 2.25 mg/m$^2$ to about 4.1 mg/m$^2$ of everolimus.

14. The method of claim 1, wherein the reduced starting dose of everolimus administered in step (a) is about 2.25 mg/m$^2$.

15. The method of claim 1, further comprising treating generalized seizures in the human.

16. The method of claim 15, wherein the generalized seizures are tonic-clonic, tonic, clonic or atonic seizures.

17. The method of claim 1, further comprising treating focal seizures in the human.

18. The method of claim 17, wherein the focal seizures are focal motor seizures without impairment of consciousness or awareness; focal seizures with impairment of consciousness or awareness; or focal seizures evolving to bilateral generalized convulsive seizures and generalized seizures.

19. The method of claim 1, which reduces the total number of seizures compared to the number of seizures experienced during a baseline period before cannabidiol was administered in the human.

20. The method of claim 19, wherein the number seizures is reduced by at least 50% compared to the number of seizures experienced during a baseline period before cannabidiol was administered in the human.

21. The method of claim 1, wherein step (c) comprises increasing the reduced starting dose of everolimus administered in step (a) to a dose that achieves a blood plasma trough concentration of everolimus ranging from 5-15 ng/mL.

22. The method of claim 1, wherein the reduced starting dose of everolimus administered in step (a) comprises administering 5 mg/m$^2$ or 4.5 mg/m$^2$ of everolimus every other day.

23. The method of claim 21, wherein the reduced starting dose of everolimus administered in step (a) ranges from about 2.5 mg/m$^2$ to about 4.5 mg/m$^2$ of everolimus.

24. The method of claim 21, wherein the reduced starting dose of everolimus administered in step (a) is about 2.5 mg/m$^2$.

25. The method of claim 21, wherein the reduced starting dose of everolimus administered in step (a) comprises administering 5 mg/m$^2$ or 4.5 mg/m$^2$ of everolimus every other day.

* * * * *